United States Patent [19]

Christensen et al.

[11] Patent Number: 4,902,339

[45] Date of Patent: Feb. 20, 1990

[54] HERBICIDAL SULFONAMIDES

[75] Inventors: Joel R. Christensen, Wilmington; Morris P. Rorer, Newark, both of Del.

[73] Assignee: E. I. Du Pont de Nemours and Company, Wilmington, Del.

[21] Appl. No.: 238,099

[22] Filed: Aug. 30, 1988

Related U.S. Application Data

[60] Division of Ser. No. 842,295, Mar. 26, 1986, Pat. No. 4,801,327, which is a continuation-in-part of Ser. No. 739,232, May 30, 1985, abandoned.

[51] Int. Cl.$^4$ ............... C07D 401/12; C07D 403/12; A01N 43/66; A01N 43/70
[52] U.S. Cl. ............................ 71/93; 71/90; 71/91; 544/113; 544/219; 544/211; 544/212; 544/206; 544/207; 544/208; 544/209; 544/96; 544/3; 544/197; 544/198
[58] Field of Search ............... 71/90, 91, 93; 544/113, 544/219, 211, 212, 206, 207, 208, 209, 96, 3, 197, 198

[56] References Cited

U.S. PATENT DOCUMENTS

| | | | |
|---|---|---|---|
| 4,127,405 | 11/1978 | Levitt | 71/93 |
| 4,169,719 | 10/1979 | Levitt | 71/92 |
| 4,475,944 | 10/1984 | Rorer | 71/90 |
| 4,492,599 | 1/1985 | Levitt et al. | 71/93 |
| 4,602,936 | 7/1986 | Töpfl et al. | 71/90 |
| 4,655,817 | 4/1987 | Thompson | 71/90 |
| 4,657,578 | 4/1987 | Thompson | 71/90 |
| 4,662,931 | 5/1987 | Thompson | 71/90 |
| 4,664,695 | 5/1987 | Schurter et al. | 71/92 |
| 4,668,279 | 5/1987 | Rorer | 71/92 |
| 4,690,705 | 9/1987 | Christensen | 71/90 |
| 4,699,647 | 10/1987 | Rorer | 71/90 |
| 4,699,649 | 10/1987 | Rorer | 71/90 |
| 4,705,558 | 11/1987 | Hartzell | 71/92 |
| 4,756,742 | 7/1988 | Thompson | 71/90 |
| 4,762,550 | 8/1988 | Hartzell | 71/94 |

FOREIGN PATENT DOCUMENTS

| | | |
|---|---|---|
| 83975 | 7/1983 | European Pat. Off. . |
| 85476 | 8/1983 | European Pat. Off. . |
| 101670 | 4/1984 | European Pat. Off. . |
| 116518 | 8/1984 | European Pat. Off. . |
| 141777 | 6/1985 | European Pat. Off. . |
| 161211 | 11/1985 | European Pat. Off. . |
| 63-194795 | 3/1988 | Japan . |
| 830441 | 7/1983 | South Africa . |
| 838416 | 5/1984 | South Africa . |

OTHER PUBLICATIONS

Chemical Abstracts, vol. 100, No. 25, p. 604, Abstract No. 209882, (1984).

Primary Examiner—John M. Ford

[57] ABSTRACT

The invention relates to certain sulfonylurea compounds having a carbocyclic or heterocyclic ring ortho to the sulfonylurea linkage, compositions thereof and a method of their use as herbicides or plant growth regulants.

30 Claims, No Drawings

HERBICIDAL SULFONAMIDES

This is a division of application U.S. Ser. No. 842,295 filed Mar. 26, 1986, which is now U.S. Pat. No. 4,801,327 which is a continuation-in-part of U.S. Ser. No. 739,232 filed May 30, 1985, which is now abandoned.

BACKGROUND OF THE INVENTION

The invention relates to certain sulfonylurea compounds having a carbocyclic or heterocyclic ring linked indirectly ortho to the sulfonylurea linkage, compositions thereof and a method of their use as herbicides or plant growth regulants.

New compounds effective for controlling the growth of undesired vegetation are in constant demand. In the most common situation, such compounds are sought to selectively control the growth of weeds in useful crops such as cotton, rice, corn, wheat and soybeans, to name a few. Unchecked weed growth in such crops can cause significant losses, reducing profit to the farmer and increasing costs to the consumer. In other situations, herbicides are desired which will control all plant growth. Examples of areas in which complete control of all vegetation is desired are areas around fuel storage tanks, ammunition depots and industrial storage areas. There are many products commercially available for these purposes, but the search continues for products which are more effective, less costly and environmentally safe.

U.S. Pat. Nos. 4,127,405 and 4,169,719 disclose herbicidal benzenesulfonylureas.

European patent application (EP-A) No. 83,975, published July 20, 1983, discloses herbicidal benzenesulfonamides of formula

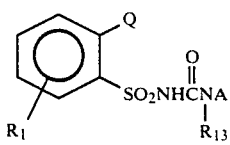

wherein
Q is selected from various five or six-membered aromatic or partially unsaturated heterocyclic rings containing 2 or 3 heteroatoms selected from O, S or NR.

European patent application (EP-A) No. 85/476, published Aug. 10, 1983, discloses herbicidal benzenesulfonamides of formulae

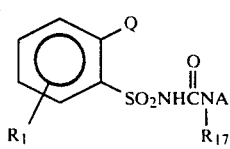

and

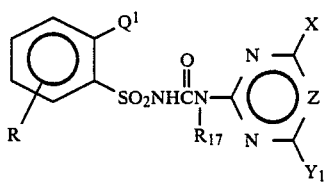

wherein
Q is selected from various 5-membered aromatic heterocycles, and their dihydro and tetrahydro analogs, which contain one heteroatom selected from O, S or NR, or Q is a saturated or partially unsaturated 6-membered ring containing one heteroatom selected from O or S; and
$Q^1$ is a 6-membered aromatic heterocycle containing one to three N atoms.

South African patent application No. 83/8416, published May 12, 1984, discloses herbicidal benzenesulfonamides of formula

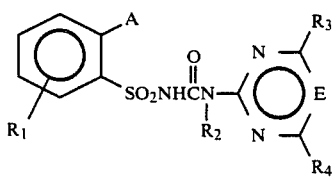

wherein
A is an unsaturated or only partially saturated 5- or 6-membered heterocyclic ring system which is bonded through a carbon atom and contains 1, 2 or 3 heteroatoms.

European patent application No. 116,518, published Aug. 22, 1984, discloses herbicidal sulfonamides of formula

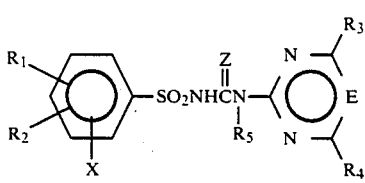

wherein
X is $NR_6R_7$, $N(SO_2R_9)_2$ or

A is CO, $SO_2$, $CONR_{23}$ or $CO_2$;
B is $C_1$–$C_4$ alkyl or $C_2$–$C_4$ alkenyl; and
C is CO, $CR_{21}R_{22}$ or $SO_2$.

U.S. Pat. No. 4,475,944 discloses herbicidal sulfamates, possessing an ortho-heterocyclic ring, such as those of formula

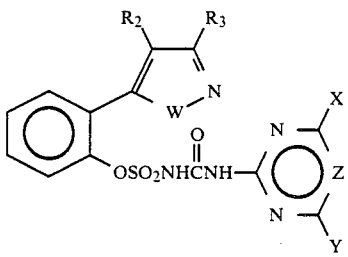

wherein
W is O, S or NR₁.

European patent application (EP-A) No. 141,777 (Swiss priority 9/9/83, published 6/15/85) discloses herbicidal sulfonamides of formula

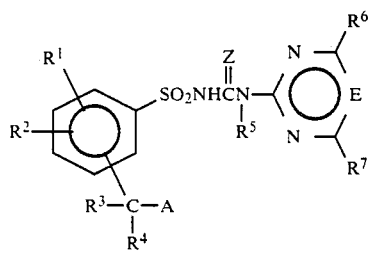

wherein
$R^3$ is H, $C_1$-$C_4$ alkyl, $C_1$-$C_4$ haloalkyl or CN;
$R^4$ is H or $C_1$-$C_4$ alkyl;
A is $Y(CH_2)_nR^{17}$ or

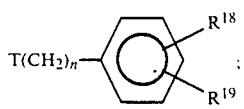

$R^{17}$ is a 5-6-membered heterocyclic radical;
Y is O, S or a direct bond; and
n is 0 or 1.

South African patent application No. 83/0441 (Swiss priority 1/25/82) discloses herbicidal benzenesulfonamides of formula

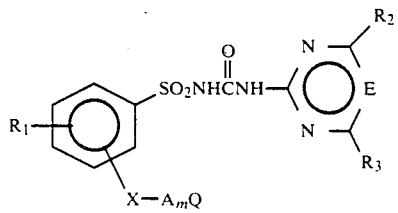

wherein
$R_1$ is H, halogen, $NO_2$, $C_1$-$C_4$ haloalkyl,
$C_1$-$C_4$ alkyl, $C_1$-$C_4$ alkoxy, $C_2$-$C_5$ alkenyl or $C_1$-$C_4$ alkoxycarbonyl;
$R_2$ is $C_1$-$C_3$ alkyl or $C_1$-$C_3$ alkoxy, each unsubstituted or substituted by 1 to 3 halogen atoms;
$R_3$ is halogen, H, $NR_4R_5$, $C_1$-$C_3$ alkyl, unsubstituted or substituted by 1 to 3 halogen atoms or $C_1$-$C_4$ alkoxy, or is $C_1$-$C_3$ alkoxy, unsubstituted or substituted by methoxy, ethoxy, or 1 to 3 halogen atoms;
A is $C_1$-$C_4$ alkylene or $C_2$-$C_4$ alkenylene, each unsubstituted or substituted by $C_1$-$C_4$ alkyl;

m is 0 or 1;
E is N or CH;
X is oxygen, sulfur, SO or $SO_2$; and
Q is, in part, a 5- or 6-membered heterocyclic ring or a fused homologue thereof, each linked through a carbon atom to the bridge —X—A$_m$— or, if the heterocyclic ring contains nitrogen, is also bound through a nitrogen atom, and which is unsubstituted or mono- to trisubstituted by halogen, cyano, nitro, $C_1$-$C_4$ alkyl, $C_1$-$C_4$ alkoxy, $C_1$-$C_4$ alkylthio, $C_2$-$C_5$ alkenyl, $C_1$-$C_4$ haloalkyl, $C_1$-$C_4$ alkoxycarbonyl, —$NR_{15}R_{16}$ or —SO—$NR_{17}R_{18}$.

SUMMARY OF THE INVENTION

Now new herbicidal compounds and compositions thereof have been found that function as preemergent or postemergent herbicides or as plant growth regulants. The compounds of the invention are compounds of Formula I

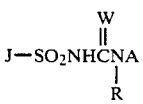

wherein
J is

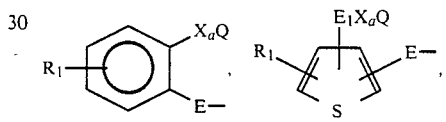

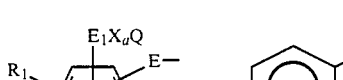

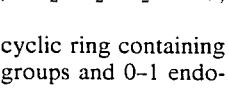

W is O or S;
R is H or $CH_3$;
$E_1$ is O, S, SO, $SO_2$ or a single bond;
$X_a$ is $CH_2$, $CH(CH_3)$, $CH_2CH_2$, $CH_2CH_2CH_2$ or CO;
E is a single bond, $CH_2$ or O;
Q is a 5- or 6-membered carbocyclic ring containing either one or two carbonyl groups and 0-1 endocyclic double bonds; a 5-membered heterocyclic ring, containing 2-4 atoms of carbon and 1-3 heteroatoms selected from the group consisting of 0-2 oxygen, 0-2 sulfur or 0-3 nitrogen, wherein sulfur may take the form of S, SO or $SO_2$, and containing one or two carbonyl or sulfonyl ($SO_2$) groups, or one carbonyl and one sulfonyl group and 0-1 endocyclic double bonds; or a 6-membered heterocyclic ring, containing 2-5 atoms of carbon and 1-3 heteroatoms selected from the group consisting of 0-2 oxygen, 0–2 sulfur or 0–3 nitrogen, wherein sulfur may take the form of S, SO or $SO_2$, and containing one or two carbonyl or sulfonyl ($SO_2$) groups, or one carbonyl and one sulfonyl group and 0–2 endocyclic double bonds; said Q value may further be optionally substituted with 1–2 substituent groups; substituents on carbon may be selected from the group consisting of halogen, $C_1$–$C_4$ alkyl, $C_1$–$C_4$ haloalkyl, $CH_2(C_2$–$C_3$ alkenyl), $CH_2(C_2$–$C_3$ alkynyl), $C_2$–$C_4$ alkoxycarbonyl, CN, OH, $C_1$–$C_3$ alkoxy, $C_1$–$C_3$ alkylthio, $C_1$–$C_3$ alkylsulfinyl, $C_1$–$C_3$ alkylsulfonyl or $C_2$–$C_4$ alkylcarbonyl; substituents on nitrogen may be selected from the group consisting of $C_1$–$C_4$ alkyl, $C_1$–$C_4$ haloalkyl, $CH_2(C_2$–$C_3$ alkenyl), $CH_2(C_2C_3$ alkynyl), $C_2$–$C_4$ alkoxycarbonyl or $C_2$–$C_4$ alkylcarbonyl;

$R_1$ is H, $C_1$–$C_3$ alkyl, $C_1$–$C_3$ haloalkyl, halogen, nitro, $C_1$–$C_3$ alkoxy, $SO_2NR_aR_b$, $C_1$–$C_3$ alkylthio, $C_1$–$C_3$ alkylsulfinyl, $C_1$–$C_3$ alkylsulfonyl, $CH_2CN$, CN, $CO_2R_c$, $C_1$–$C_3$ haloalkoxy, $C_1$–$C_3$ haloalkylthio, $C_2$–$C_4$ alkoxyalkyl, $C_2$–$C_4$ alkylthioalkyl, $CH_2N_3$ or $NR_dR_e$;

$R_a$ is H, $C_1$–$C_4$ alkyl, $C_2$–$C_3$ cyanoalkyl, methoxy or ethoxy;

$R_b$ is H, $C_1$–$C_4$ alkyl or $C_3$–$C_4$ alkenyl; or $R_a$ and $R_b$ may be taken together as —$(CH_2)_3$—, —$(CH_2)_4$—, —$(CH_2)_5$— or —$CH_2CH_2OCH_2CH_2$—;

$R_c$ is $C_1$–$C_4$ alkyl, $C_3$–$C_4$ alkenyl, $C_3$–$C_4$ alkynyl, $C_2$–$C_4$ haloalkyl, $C_2$–$C_3$ cyanoalkyl, $C_5$–$C_6$ cycloalkyl, $C_4$–$C_7$ cycloalkylalkyl or $C_2$–$C_4$ alkoxyalkyl;

$R_d$ and $R_e$ are independently H or $C_1$–$C_2$ alkyl;

A is

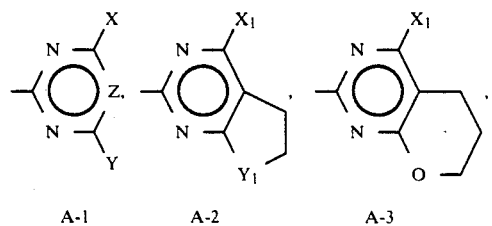

A-1    A-2    A-3

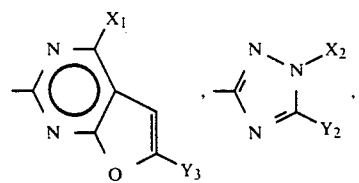

A-4    A-5

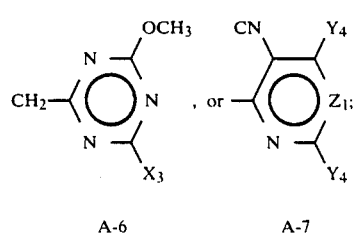

A-6    A-7

X is H, $C_1$–$C_4$ alkyl, $C_1$–$C_4$ alkoxy, $C_1$–$C_4$ haloalkoxy, $C_1$–$C_4$ haloalkyl, $C_1$–$C_4$ haloalkylthio, $C_1$–$C_4$ alkylthio, halogen, $C_2$–$C_5$ alkoxyalkyl, $C_2$–$C_5$ alkoxyalkoxy, amino, $C_1$–$C_3$ alkylamino, di($C_1$–$C_3$ alkyl)amino or $C_3$–$C_5$ cycloalkyl;

Y is H, $C_1$–$C_4$ alkyl, $C_1$–$C_4$ alkoxy, $C_1$–$C_4$ haloalkoxy, $C_1$–$C_4$ haloalkylthio, $C_1$–$C_4$ alkylthio, $C_2$–$C_5$ alkoxyalkyl, $C_2$–$C_5$ alkoxyalkoxy, amino, $C_1$–$C_3$ alkylamino, di($C_1$–$C_3$ alkyl)amino, $C_3$–$C_4$ alkenyloxy, $C_3$–$C_4$ alkynyloxy, $C_2$–$C_5$ alkylthioalkyl, $C_1$–$C_4$ haloalkyl, $C_2$–$C_4$ alkynyl, azido, cyano, $C_2$–$C_5$ alkylsulfinylalkyl, $C_2$–$C_5$ alkylsulfonylalkyl,

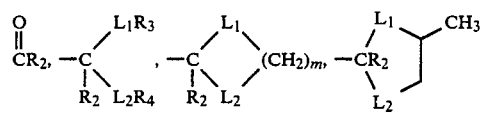

or $N(OCH_3)CH_3$;

m is 2 or 3;

$L_1$ and $L_2$ are independently O or S;

$R_2$ is H or $C_1$–$C_3$ alkyl;

$R_3$ and $R_4$ are independently $C_1$–$C_3$ alkyl;

Z is CH, N, $CCH_3$, $CC_2H_5$, CCl or CBr;

$Z_1$ is CH or N;

$Y_1$ is O or $CH_2$;

$X_1$ is $CH_3$, $OCH_3$, $OC_2H_5$ or $OCF_2H$;

$X_2$ is $CH_3$, $C_2H_5$ or $CH_2CF_3$;

$Y_2$ is $OCH_3$, $OC_2H_5$, $SCH_3$, $SC_2H_5$, $CH_3$ or $CH_2CH_3$;

$X_3$ is $CH_3$ or $OCH_3$;

$Y_3$ is H or $CH_3$;

$X_4$ is $CH_3$, $OCH_3$, $OC_2H_5$, $CH_2OCH_3$ or Cl; and $Y_4$ is $CH_3$, $OCH_3$, $OC_2H_5$ or Cl;

and their agriculturally suitable salts; provided that (a) when Q contains 2 heteroatoms selected from 0–2 oxygen and 0–2 sulfur, said heteroatoms are not bonded directly to one another unless in the form O—$SO_2$, and when Q contains 3 nitrogen heteroatoms, only two of these may be bonded directly together;

(b) when X is Cl, F, Br or I, then Z is CH and Y is $OCH_3$, $OC_2H_5$, $N(OCH_3)CH_3$, $NHCH_3$, $N(CH_3)_2$ or $OCF_2H$;

(c) when X or Y is $C_1$ haloalkoxy, then Z is CH;

(d) when J is J-2 or J-3, the substituents $E_1X_aQ$ and the sulfonylurea bridge are on adjacent carbon atoms;

(e) when E is O, then J is J-1 and W is O;

(f) when W is S, then R is H, A is H, A is A-1, Z is CH or N and Y is $CH_3$, $OCH_3$, $OC_2H_5$, $CH_2OCH_3$, $C_2H_5$, $CH_3$, $SCH_3$, $OCH_2CH=CH_2$, $OCH_2C\equiv CH$, $OCH_2CH_2OCH_3$, $CH(OCH_3)_2$ or 1,3-dioxolan-2-yl;

(g) when the total number of carbon atoms of X and Y is greater than four, then the number of carbons of $R_1$ must be less than or equal to two, and the number of carbons of the substituent on Q must also be less than or equal to two;

(h) $X_4$ and $Y_4$ are not simultaneously Cl;

(i) when A is A-1 and J is J-1 wherein E is a single bond, $X_a$ is $CH_2$, $CH(CH_3)$ or $CH_2CH_2$ and Q is a 5-membered heterocyclic ring containing one endocyclic double bond or a 6-membered heterocyclic ring containing 1 or 2 endocyclic double bonds which is unsubstituted or substituted by one or more $C_1$–$C_4$ alkyl groups then said heterocycle must contain at least one nitrogen and be bound to $X_a$ through nitrogen; and (j) when $X_a$ is CO, then $E_1$ is a single bond.

Representative examples of preferred Q include:

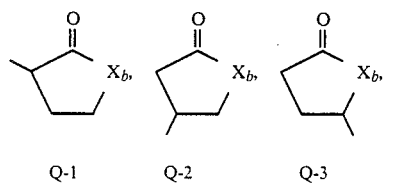
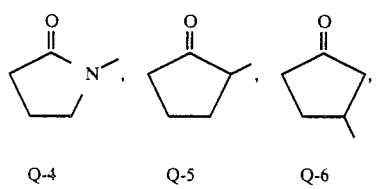
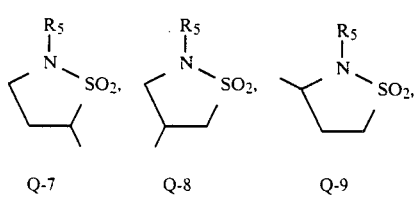
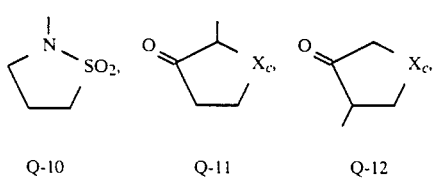
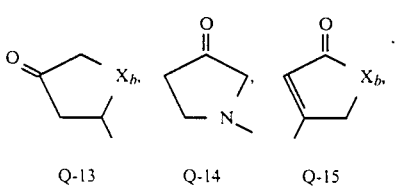
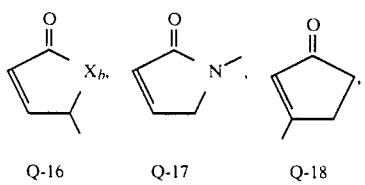
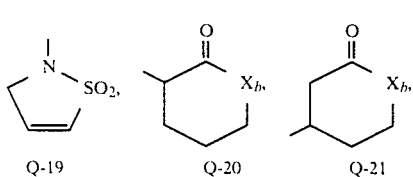
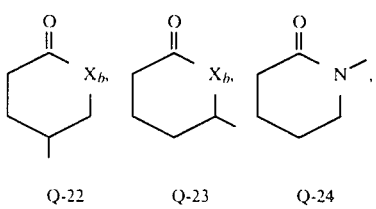
-continued
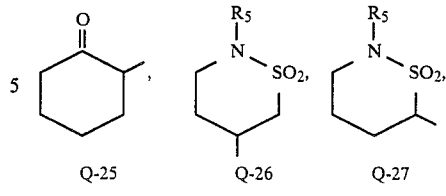
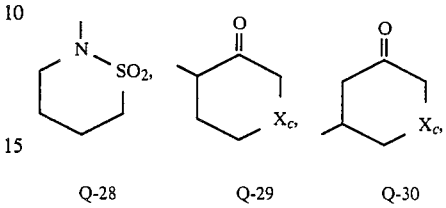
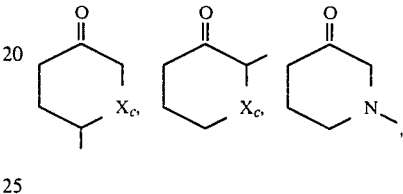
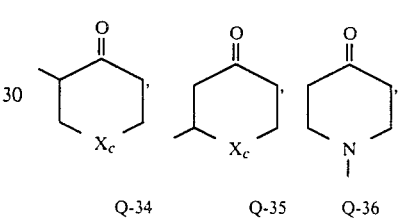
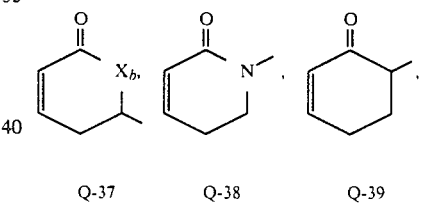
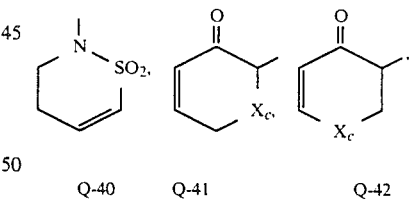
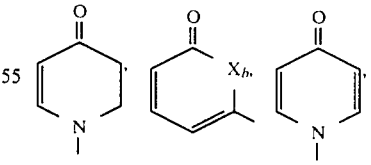
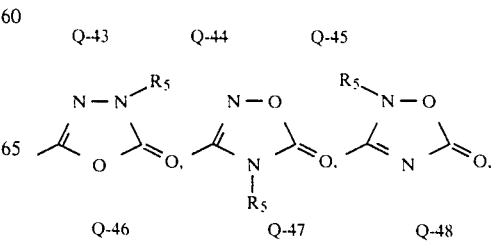

-continued

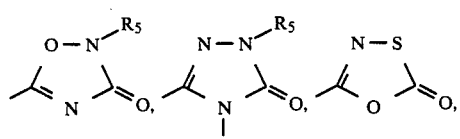

Q-49  Q-50  Q-51

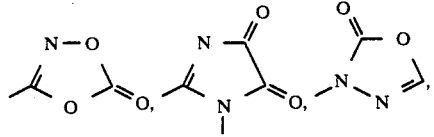

Q-52  Q-53  Q-54

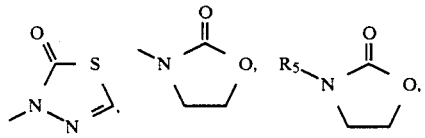

Q-55  Q-56  Q-57

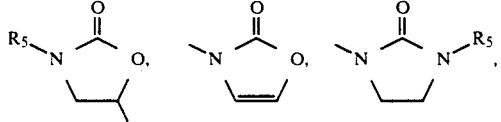

Q-58  Q-59  Q-60

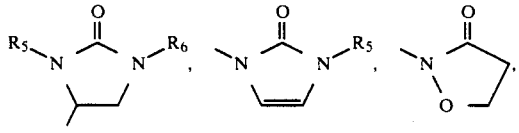

Q-61  Q-62  Q-63

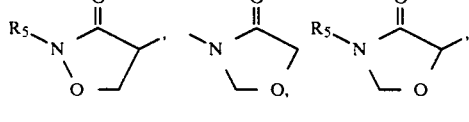

Q-64  Q-65  Q-66

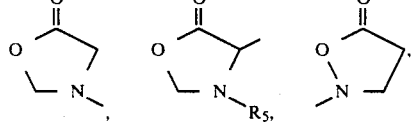

Q-67  Q-68  Q-69

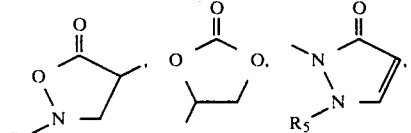

Q-70  Q-71  Q-72

-continued

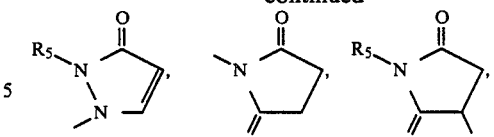

Q-73  Q-74  Q-75

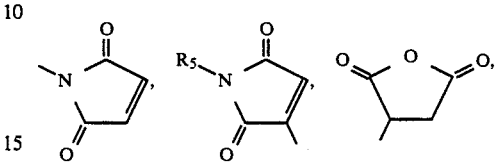

Q-76  Q-77  Q-78

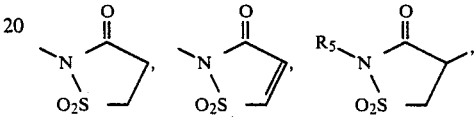

Q-79  Q-80  Q-81

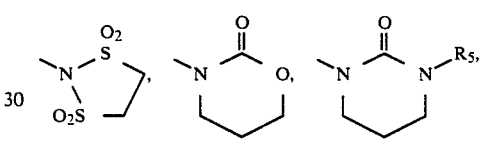

Q-82  Q-83  Q-84

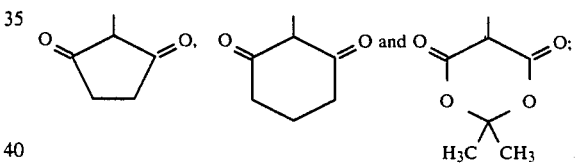

Q-85  Q-86  Q-87 wherein

Q-1 through Q-87 may be optionally substituted with 1 or 2 groups selected from $C_1$-$C_2$ alkyl or $C_1$-$C_2$ haloalkyl;

$R_5$ and $R_6$ are independently H or $C_1$-$C_3$ alkyl;

$X_b$ is O or $NR_5$; and $X_c$ is O, S, SO, $SO_2$ or $NR_5$.

In the above definitions, the term "alkyl", used either alone or in compound words such as "alkylthio" or "haloalkyl", denotes straight chain or branched alkyl, e.g. methyl, ethyl, n-propyl, isopropyl or the different butyl, pentyl, hexyl, heptyl, octyl, nonyl or decyl isomers.

Alkoxy denotes methoxy, ethoxy, n-propoxy, isopropyloxy and the different butyl isomers.

Alkenyl denotes straight chain or branched alkenes, e.g. vinyl, 1-propenyl, 2-propenyl, 3-propenyl and the different butenyl isomers.

Alkynyl denotes straight chain or branch alkynes, e.g., ethynyl, 1-propynyl, 2-propynyl and the different butynyl isomers.

Alkylsulfonyl denotes methylsulfonyl, ethylsulfonyl and the different propylsulfonyl isomers.

Alkylthio, alkylsulfinyl, alkylamino, alkylsulfamoyl, etc. are defined in an analogous manner.

Cycloalkyl denotes cyclopropyl, cyclobutyl, cyclopentyl and cyclohexyl.

The term "halogen", either alone or in compound words such as "haloalkyl", denotes fluorine, chlorine, bromine or iodine. Further, when used in compound words such as "haloalkyl" said alkyl may be partially halogenated or fully substituted with halogen atoms which may be the same or different. Examples of haloalkyl include $CH_2CH_2F$, $CF_2CH_3$ and $CH_2CHFCl$.

Alkylcarbonyl denotes acetyl, propionyl, and the different butyryl isomers.

Alkoxycarbonyl denotes methoxycarbonyl, ethoxycarbonyl, propoxycarbonyl and isopropoxycarbonyl.

The total number of carbon atoms in a substituent group is indicated by the $C_i$–$C_j$ prefix where i and j are numbers from 1 to 10. For example, $C_2$ cyanoalkyl would designate $CH_2CN$, $C_3$ cyanoalkyl would designate $CH_2CH_2CN$ and $CH(CN)CH_3$, and $C_2$–$C_3$ alkylthioalklyl would designate $CH_2SCH_3$, $CH_2SC_2H_5$, $CH_2CH_2SCH_3$ or $CH(CH_3)SCH_3$, and $C_2$–$C_5$ alkoxyalkoxy would represent $OCH_2OCH_3$ through $O(CH_2)_4OCH_3$ or $OCH_2O(CH_2)_3CH_3$ and the various structural isomers embraced therein.

Preferred for reasons of increased ease of synthesis and/or greater herbicidal efficacy are:
1. Compounds of Formula I where E is a single bond and Z is CH or N;
2. Compounds of Formula I where E is $CH_2$, W is O, Z is CH or N and $E_1$ is a single bond;
3. Compounds of Formula I where E is O, Z is CH or N and $E_1$ is a single bond.
4. Compounds of Preferred 1 where Q is Q-1 to Q-87; wherein
   Q-1 through Q-87 may be optionally substituted with 1 or 2 groups selected from $C_1$–$C_2$ alkyl or $C_1$–$C_2$ haloalkyl;
   $R_5$ and $R_6$ are independently H or $C_1$–$C_3$ alkyl;
   $X_b$ is O or $NR_5$; and
   $X_c$ is O, S, SO, $SO_2$ or $NR_5$.
5. Compounds of Preferred 4 where
   W is O;
   $E_1$ is a single bond;
   $X_a$ is $CH_2$ or $CH_2CH_2$;
   R is H;
   $R_1$ is H, F, Cl, Br, $C_1$–$C_2$ alkyl, $C_1$–$C_3$ alkoxy, $C_1$–$C_3$ alkylthio, or $C_1$–$C_2$ alkyl, $C_1$–$C_3$ alkoxy or $C_1$–$C_3$ alkylthio substituted with 1–3 atoms of F, Cl or Br;
   X is $C_1$–$C_2$ alkyl, $C_1$–$C_2$ alkoxy, Cl, F, Br, I, $OCF_2H$, $CH_2F$, $CF_3$, $OCH_2CH_2F$, $OCH_2CHF_2$, $OCH_2CF_3$, $CH_2Cl$ or $CH_2Br$; and
   Y is H, $C_1$–$C_2$ alkyl, $C_1$–$C_2$ alkoxy, $CH_2OCH_3$, $CH_2OCH_2CH_3$, $NHCH_3$, $N(OCH_3)CH_3$, $N(CH_3)_2$, $CF_3$, $SCH_3$, $OCH_2CH{=}CH_2$, $OCH_2C{\equiv}CH$, $OCH_2CH_2OCH_3$, $CH_2SCH_3$,

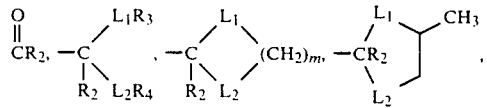

$OCF_2H$, $SCF_2H$, cyclopropyl, $C{\equiv}CH$ or $C{\equiv}CCH_3$;
6. Compounds of Preferred 5 where A is A-1;
7. Compounds of Preferred 6 where J is J-1;
8. Compounds of Preferred 6 where J is J-2;
9. Compounds of Preferred 6 where J is J-3;
10. Compounds of Preferred 6 where J is J-4;
11. Compounds of Preferred 6 where J is J-5;
12. Compounds of Preferred 6 where
    J is J-1;
    $R_1$ is H, Cl, $CH_3$ or $OCH_3$;
    X is $CH_3$, $OCH_3$, Cl or $OCF_2H$; and
    Y is $CH_3$, $OCH_3$, $C_2H_5$, $CH_2OCH_3$, $NHCH_3$, $CH(OCH_3)_2$ or cyclopropyl;
13. Compounds of Preferred 12 where Q is Q-1;
14. Compounds of Preferred 12 where Q is Q-2;
15. Compounds of Preferred 12 where Q is Q-3;
16. Compounds of Preferred 12 where Q is Q-4;
17. Compounds of Preferred 12 where Q is Q-5;
18. Compounds of Preferred 12 where Q is Q-6;
19. Compounds of Preferred 12 where Q is Q-7;
20. Compounds of Preferred 12 where Q is Q-8;
21. Compounds of Preferred 12 where Q is Q-9;
22. Compounds of Preferred 12 where Q is Q-10;
23. Compounds of Preferred 12 where Q is Q-11;
24. Compounds of Preferred 12 where Q is Q-12;
25. Compounds of Preferred 12 where Q is Q-13;
26. Compounds of Preferred 12 where Q is Q-14;
27. Compounds of Preferred 12 where Q is Q-15;
28. Compounds of Preferred 12 where Q is Q-16;
29. Compounds of Preferred 12 where Q is Q-17;
30. Compounds of Preferred 12 where Q is Q-18;
31. Compounds of Preferred 12 where Q is Q-19;
32. Compounds of Preferred 12 where Q is Q-20;
33. Compounds of Preferred 12 where Q is Q-21;
34. Compounds of Preferred 12 where Q is Q-22;
35. Compounds of Preferred 12 where Q is Q-23;
36. Compounds of Preferred 12 where Q is Q-24;
37. Compounds of Preferred 12 where Q is Q-25;
38. Compounds of Preferred 12 where Q is Q-26;
39. Compounds of Preferred 12 where Q is Q-27;
40. Compounds of Preferred 12 where Q is Q-28;
41. Compounds of Preferred 12 where Q is Q-29;
42. Compounds of Preferred 12 where Q is Q-30;
43. Compounds of Preferred 12 where Q is Q-31;
44. Compounds of Preferred 12 where Q is Q-32;
45. Compounds of Preferred 12 where Q is Q-33;
46. Compounds of Preferred 12 where Q is Q-34;
47. Compounds of Preferred 12 where Q is Q-35;
48. Compounds of Preferred 12 where Q is Q-36;
49. Compounds of Preferred 12 where Q is Q-37;
50. Compounds of Preferred 12 where Q is Q-38;
51. Compounds of Preferred 12 where Q is Q-39;
52. Compounds of Preferred 12 where Q is Q-40;
53. Compounds of Preferred 12 where Q is Q-41;
54. Compounds of Preferred 12 where Q is Q-42;
55. Compounds of Preferred 12 where Q is Q-43;
56. Compounds of Preferred 12 where Q is Q-44;
57. Compounds of Preferred 12 where Q is Q-45;
58. Compounds of Preferred 12 where Q is Q-46;
59. Compounds of Preferred 12 where Q is Q-47;
60. Compounds of Preferred 12 where Q is Q-48;
61. Compounds of Preferred 12 where Q is Q-49;
62. Compounds of Preferred 12 where Q is Q-50;
63. Compounds of Preferred 12 where Q is Q-51;
64. Compounds of Preferred 12 where Q is Q-52;
65. Compounds of Preferred 12 where Q is Q-53;
66. Compounds of Preferred 12 where Q is Q-54;
67. Compounds of Preferred 12 where Q is Q-55;
68. Compounds of Preferred 12 where Q is Q-56;
69. Compounds of Preferred 12 where Q is Q-57;
70. Compounds of Preferred 12 where Q is Q-58;
71. Compounds of Preferred 12 where Q is Q-59;
72. Compounds of Preferred 12 where Q is Q-60;
73. Compounds of Preferred 12 where Q is Q-61;

74. Compounds of Preferred 12 where Q is Q-62;
75. Compounds of Preferred 12 where Q is Q-63;
76. Compounds of Preferred 12 where Q is Q-64;
77. Compounds of Preferred 12 where Q is Q-65;
78. Compounds of Preferred 12 where Q is Q-66;
79. Compounds of Preferred 12 where Q is Q-67;
80. Compounds of Preferred 12 where Q is Q-68;
81. Compounds of Preferred 12 where Q is Q-69;
82. Compounds of Preferred 12 where Q is Q-70;
83. Compounds of Preferred 12 where Q is Q-71;
84. Compounds of Preferred 12 where Q is Q-72;
85. Compounds of Preferred 12 where Q is Q-73;
86. Compounds of Preferred 12 where Q is Q-74;
87. Compounds of Preferred 12 where Q is Q-75;
88. Compounds of Preferred 12 where Q is Q-76;
89. Compounds of Preferred 12 where Q is Q-77;
90. Compounds of Preferred 12 where Q is Q-78;
91. Compounds of Preferred 12 where Q is Q-79;
92. Compounds of Preferred 12 where Q is Q-80;
93. Compounds of Preferred 12 where Q is Q-81;
94. Compounds of Preferred 12 where Q is Q-82;
95. Compounds of Preferred 12 where Q is Q-83;
96. Compounds of Preferred 12 where Q is Q-84;
97. Compounds of Preferred 12 where Q is Q-85;
98. Compounds of Preferred 12 where Q is Q-86;
99. Compounds of Preferred 12 where Q is Q-87;
100. Compounds of Preferred 2 where
  R is H;
  J is J-1;
  $R_1$ is H;
  A is A-1;
  X is $CH_3$, $OCH_3$, $OCH_2CH_3$, Cl or $OCF_2H$;
  Y is $CH_3$, $OCH_3$, $C_2H_5$, $CH_2OCH_3$, $NHCH_3$, $CH(OCH_3)_2$ or cyclopropyl; Z is CH or N; and Q is Q-1, Q-4, Q-5, Q-7, Q-10, Q-11, Q-12, Q-17, Q-19, Q-20, Q-24, Q-25, Q-27, Q-28, Q-36, Q-38, Q-46, Q-47, Q-54, Q-56, Q-59, Q-60, Q-63, Q-71, Q-74, Q-76, Q-78 and Q-79;
101. Compounds of Preferred 3 where
  R is H;
  $R_1$ is H;
  A is A-1;
  X is $CH_3$, $OCH_3$, $OCH_2CH_3$, Cl or $OCF_2H$;
  Y is $CH_3$, $OCH_3$, $C_2H_5$, $CH_2OCH_3$, $NHCH_3$, $CH(OCH_3)_2$ or cyclopropyl; Z is CH or N; and Q is Q-1, Q-4, Q-5, Q-7, Q-10, Q-11, Q-12, Q-17, Q-19, Q-20, Q-24, Q-25, Q-27, Q-28, Q-36, Q-38, Q-46, Q-47, Q-54, Q-56, Q-59, Q-60, Q-63, Q-71, Q-74, Q-76, Q-78 and Q-79.
102. Compounds of Formula L wherein
  $E_1$ is a single bond.
  $X_a$ is $CH_2$, $CH(CH_3)$, $CH_2CH_2$ or $CH_2CH_2CH_2$;
  Q is a saturated or partially saturated 5- or 6-membered carbocyclic ring, containing either one or two carbonyl groups, or a saturated or partially saturated 5- or 6-membered heterocyclic ring, containing 2-5 atoms of carbon and 1-3 heteroatoms selected from the group consisting of 0-2 oxygen, 0-2 sulfur or 0-3 nitrogen, wherein sulfur may take the form of S, SO or $SO_2$, and containing one or two carbonyl or sulfonyl ($SO_2$) groups, or one carbonyl and one sulfonyl group; Q may further be optionally substituted with 1-2 substituent groups; substituents on carbon may be selected from the group consisting of halogen, $C_1$–$C_4$ alkyl, $C_1$–$C_4$ haloalkyl, $CH_2(C_2$–$C_3$ alkenyl), $CH_2(C_2$–$C_3$ alkynyl), $C_2$–$C_4$ alkoxycarbonyl, CN, OH, $C_1$–$C_3$ alkoxy, $C_1$–$C_3$ alkylthio, $C_1$–$C_3$ $C_1$–$C_3$ alkylsulfinyl, $C_1$–$C_3$ alkylsulfonyl or $C_2$–$C_4$ alkylcarbonyl, substituents on nitrogen may be selected from the group consisting of $C_1$–$C_4$ alkyl, $C_1$–$C_4$ haloalkyl, $CH_2(C_2$–$C_3$ alkenyl), $CH_2(C_2$–$C_3$ alkynyl), $C_2$–$C_4$ alkoxycarbonyl or $C_2$–$C_4$ alkylcarbonyl;
  $R_1$ is H, $C_1$–$C_3$ alkyl, $C_1$–$C_3$ haloalkyl, halogen, nitro, $C_1$–$C_3$ alkoxy, $SO_2NR_aR_b$, $C_1$–$C_3$ alkylthio, $C_1$–$C_3$ alkylsulfinyl, $C_1$–$C_3$ alkylsulfonyl, $CH_2CN$, CN, $CO_2R_c$, $C_1$–$C_3$ haloalkoxy or $C_1$–$C_3$ haloalkylthio;
  A is

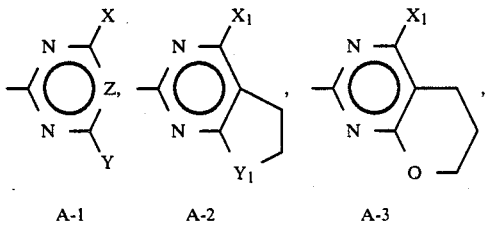

A-1   A-2   A-3

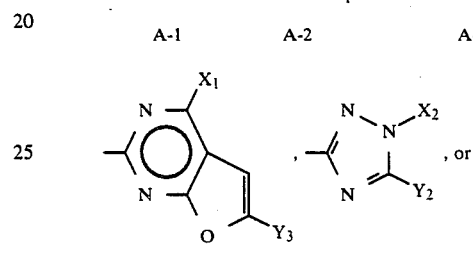

A-4   A-5

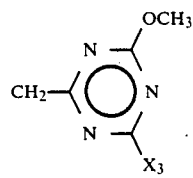

A-6

Specifically Preferred for reasons of greatest ease of synthesis and/or greatest herbicidal efficacy are:

N-[(4,6-dimethoxypyrimidin-2-yl)aminocarbonyl]-2-(2-oxo-1-pyrrolidinylmethyl)benzenesulfonamide, m.p. 185°–187° C.;

N-[(4,6-dimethoxy-1,3,5-triazin-2-yl)aminocarbonyl]-2-(2-oxo-1-pyrrolidinylmethyl)benzenesulfonamide, m.p. 194°–195° C.;

N-[(4,6-dimethoxypyrimidin-2-yl)aminocarbonyl]-2-(2-oxo-3-oxazolidinylmethyl)-3-thiophenesulfonamide, m.p. 157°–160° C.; and N-[(4-methoxy-6-methyl-1,3,5-triazin-2-yl)aminocarbonyl]-2-(2-oxo-3-oxazolidinylmethyl)-3-thiophenesulfonamide, m.p. 155°–161° C.

DETAILED DESCRIPTION OF THE INVENTION

Synthesis

Compounds of Formula I, wherein E is $CH_2$ or a single bond, can be synthesized by one or more of the procedures outlined in Equation 1.

Equation 1

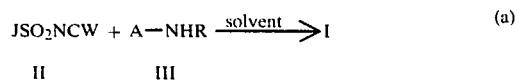

II    III

-continued
Equation 1

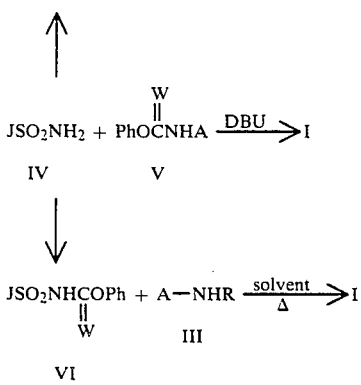

wherein

J, R, and A are as previously defined, provided E is CH$_2$ or a single bond.

The reaction of Equation 1a can be carried out according to procedures described in U.S. Pat. No. 4,127,405.

The sulfonyl isocyanates II are prepared from the corresponding sulfonamides of Formula IV according to procedures described in U.S. Pat. No. 4,238,621 or by the procedure of H. Ulrich, B. Tucker, and A. Sayigh, *J. Org. Chem.*, 34, 3200 (1969).

Sulfonyl isothiocyanates (II, W is S) are known in the art and are prepared from the corresponding sulfonamides (IV) by reaction with carbon disulfide and potassium hydroxide followed by treatment of the resulting dipotassium salt VI with phosgene. Such a procedure is described in *Arch. Pharm.* 299, 174 (1966).

Alternatively compounds of Formula I can be prepared according to Equation 1b or by the reaction of Equation 1c as described in U.S. Pat. No. 4,443,243.

The sulfonylureas of Formula I, wherein E is O, can be prepared by one or both of the procedures described in Equation 2.

Equation 2

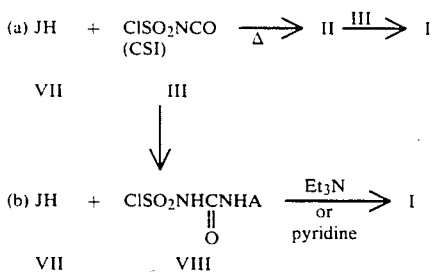

wherein

J is as previously defined, provided E is O.

Phenols of Formula VII react with chlorsulfonylisocyanate (CSI) under elevated temperatures (Equation 2a) to provide the sulfonyl isocyanates II, which react with heterocyclic amines of Formula III to yield the sulfonylureas I according to the procedure in U.S. Pat. No. 4,475,944. Alternatively, the reaction of Equation 2b may be employed according to the procedure described in U.S. Pat. No. 4,391,976.

Agriculturally suitable salts of compounds of Formula I are also useful herbicides and can be prepared in a number of ways known to the art. For example, metal salts can be made by contacting compounds of Formula I with a solution of an alkali or alkaline earth metal salt having a sufficiently basic anion (e.g., hydroxide, alkoxide or carbonate).

Quaternary amine salts can be made by similar techniques.

Salts of compounds of Formula I can also be prepared by exchange of one cation for another. Cationic exchange can be effected by direct contact of an aqueous solution of a salt of a compound of Formula I (e.g., alkali or quaternary amine salt) with a solution containing the cation to be exchanged. This method is most effective when the desired salt containing the exchanged cation is insoluble in water and can be separated by filtration.

Exchange may also be effected by passing an aqueous solution of a salt of a compound of Formula I (e.g., an alkali metal or quaternary amine salt) through a column packed with a cation exchange resin containing the cation to be exchanged for that of the original salt and the desired product is eluted from the column. This method is particularly useful when the desired salt is water-soluble, e.g., a potassium, sodium or calcium salt.

Acid addition salts, useful in this invention, can be obtained by reacting a compound of Formula I with a suitable acid, e.g., p-toluenesulfonic acid, trichloroacetic acid or the like.

The synthesis of heterocyclic amines such as those represented by Formula III has been reviewed in "The Chemistry of Heterocyclic Compounds," a series published by Interscience Publ., New York and London. Aminopyrimidines are described by D. J. Brown in "The Pyrimidines," Vol. XVI of the series mentioned above which is herein incorporated by reference. The 2-amino-1,3,5-triazines of Formula III, where A is A-1 and Z is N, can be prepared according to methods described by E. M. Smolin and L. Rapaport in "s-Triazines and Derivatives," Vol. XIII.

Pyrimidines of Formula III, where A is A-1 and Y is an acetal or thioacetal substituent, can be prepared by methods taught in European patent application No. 84,224 (published July 27, 1983).

Pyrimidines of Formula III, where A is A-1 and Y is cyclopropyl of OCF$_2$H can be synthesized according to the methods taught in U.S. Pat. No. 4,515,626 and U.S. Pat. No. 4,540,782, respectively.

Compounds of Formula III, where A is A-2 or A-3, can be prepared by procedures disclosed in U.S. Pat. No. 4,339,267.

Compounds of Formula III, where A is A-4, can be prepared by methods taught in U.S. Pat. No. 4,487,626.

Additional references dealing with the synthesis of bicyclic pyrimidines of Formula III, where A is A-2, A-3, or A-4 are Braker, Sheehan, Spitzmiller and Lott, *J. Am. Chem. Soc.*, 69, 3072 (1947); Mitler and Bhattachanya, *Quart. J. Indian Chem. Soc.*, 4, 152 (1927); Shrage and Hitchings, *J. Org. Chem.*, 16, 1153 (1951); Caldwell, Kornfeld and Donnell, *J. Am Chem. Soc.*, 63, 2188 (1941); and Fissekis, Myles and Brown, *J. Org. Chem.*, 29, 2670 (1964).

Compounds of Formula III, where A is A-5, can be prepared by methods taught in U.S. Pat. No. 4,421,550.

Compounds of Formula III, where A is A-6, can be prepared by methods taught in the U.S. Pat. No. 4,496,392.

The required sulfonamides of Formula IV, provided E is not oxygen, can be conveniently prepared by amination of the corresponding sulfonyl chlorides with ammonia or ammonium hydroxide by methods known to those skilled in the art. Alternatively deprotection of N-t-butylsulfonamides with polyphosphoric acid (PPA) or trifluoroacetic acid (TFA) as described by J. D. Lombardino, *J. Org. Chem.*, 36, 1843 (1971) or J. D. Catt and W. L. Matier, *J. Org. Chem.*, 39, 566 (1974), respectively, provides compounds of Formula IV.

In addition, deprotection of N-t-butyldimethylsilyl-sulfonamides with fluoride ion, provides sulfonamides of Formula IV, wherein E is not oxygen.

The intermediate sulfonyl chlorides of Formula X, as depicted in Equation 3, can be prepared from aromatic amines via a diazotization process, as described in EPO Publication Nos. 83,975 and 85,476; or by oxidative chlorination of thiols or thioethers with chlorine and water as reviewed in Gilbert, "Sulfonation and Related Reactions," pp. 202–214, Interscience Publishers, New York, 1965; when $R_7=H$ or benzyl, the oxidative chlorination may be effected by sodium hypochlorite following procedures described by L. H. McKendry and N. R. Pearson in South African patent application No. 84/8845 (November 13, 1984); or by metal halogen exchange or directed lithiation of appropriately substituted aryl or heterocyclic substrates followed by trapping with sulfuryl chloride. The lithiation can be performed according to the procedure of S. H. Bhattacharya, et al., *J. Chem. Soc.* (C), 1265 (1968) or by procedures reviewed by H. Gscwend and H. Rodriquez in *Organic Reactions*, Vol. 26, Wiley, New York, 1979, and references cited within; or finally, when E is a $CH_2$ moiety, by a two step procedure involving the conversion of aromatic chloromethyl or bromomethyl compounds to isothiouronium salts, as described by Johnson and Sprague, *J. Am. Chem. Soc.*, 58, 1348 (1936); 59, 1837 and 2439 (1937); 61, 176 (1939), followed by oxidative chlorination by the procedure of Johnson as described in *J. Am. Chem. Soc.*, 61, 2548 (1939) to provide the sulfonyl chlorides X.

Equation 3

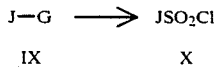

$$\begin{array}{ccc} J-G & \longrightarrow & JSO_2Cl \\ IX & & X \end{array}$$

wherein
J is as previously defined provided E is not oxygen,
G is H. $NH_2$, $SR_7$, Br, $CH_2Cl$, $CH_2Br$, and
$R_7$ is H, $C_1-C_3$ alkyl, benzyl.

Amines of the Formula IX, wherein G is $NH_2$, can be prepared from the corresponding nitro compounds by various reduction procedures as described in U.S. Pat. Nos. 3,846,440 and 3,846,439 and in EP-A No. 83,975 and references cited therein.

Phenols of Formula VII can be prepared from amines of Formula IX ($G=NH_2$) via a diazotization process, as described in A. I. Vogel, "Practical Organic Chemistry," P. 595 (1956), 3rd Ed; U.S. Pat. No. 3,270,029; J. H. Finley, et al., *J. Het. Chem.*, 6, 841 (1969); and M. Ohta, et al., *J. Pharm. Soc. Japan*, 73, 701 (1953).

Compounds of the Formula XII, which serve as intermediates to compounds of the Formula I as illustrated in Equations 1–3, can be prepared from precursors of the Formula XI by one or more of the procedures outlined below.

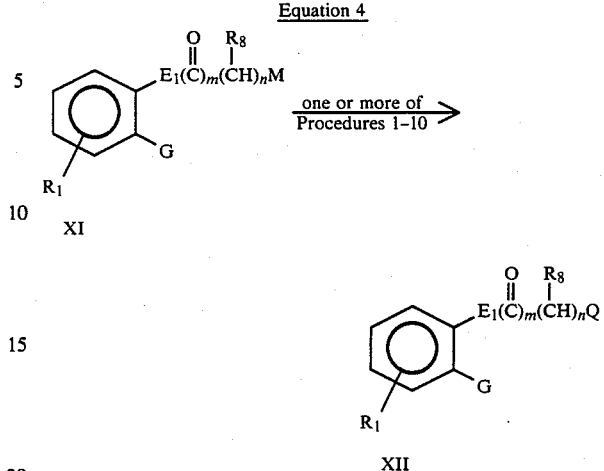

Equation 4 wherein
Q and $R_1$ are as originally defined;
$R_8$ is H or $CH_3$, provided that when n is 2 or 3, $R_8$ is H;
m is 0 or 1, provided when m=1, n must be 0;
n is 0, 1, 2, or 3, provided that m and n cannot both be 0;
G is Cl, Br, $CH_2Cl$, $CH_2Br$, OH, $NH_2$, $NO_2$, $SR_7$, $SO_2NH_2$, $SO_2NH$-t-butyl or $SO_2NHSi(CH_3)_2$-t-butyl;
M is Cl, Br, I, $NH_2$, NHOH, $NHNH_2$, $COOCH_3$, $CONHNH_2$, CN, COCl, CHO or H or suitable leaving group, provided that when m=1, M is not Br or I;
$R_7$ is H, $C_1-C_3$ alkyl or benzyl.
$E_1$ is O, S, SO, $SO_2$ or a single bond provided that when m=1, $E_1$ is a single bond.

The ten procedures are based on established literature methods precedented by the references cited in Table 2. The references cited have direct applicability to compounds of the Formula XII, wherein J is J-1. However, the procedures and experimental methods described in these references are equally applicable to the synthesis of compounds of Formula XII, wherein J is J-2 through J-5, by analogous procedures or slight modifications thereof. The chemistry of the thiophene, pyridine and pyrazole ring systems has been reviewed in "Chemistry of Heterocyclic Compounds," Volumes 3, 14, and 5, respectively. Wiley, New York 1952 and later.

It should be noted that the chemical compatibility of the wide variety of reactions and reaction conditions described throughout this disclosure with J, $R_1$, Q, and G must be taken into account and as such requires a judicious choice of the appropriate methods for preparing compounds described within this disclosure. In addition, circumvention of instances of incompatibility may be achieved by the suitable selection of a protecting group, obvious to one skilled in the art. For a compilation of references describing the wide variety of protecting groups available, see T. W. Greene, "Protective Groups in Organic Synthesis," John Wiley and Sons, Inc., New York, 1981.

The synthesis of the starting materials of Formula XI are known in the general literature or can be prepared, by those skilled in the art, by simple modifications of established routes.

Procedure 1: Direct N-alkylation of intact heterocyclic compounds, containing an N—H moiety, with compound substrates of the Formula XI, wherein m=0 and M is Cl, Br, or Iodine; or N-benzoylation of heterocyclic, containing an N—H moiety, with benzoyl chlorides of the form XI, wherein m=1, M is Cl, and G is Cl, Br, $CH_2Cl$, $CH_2Br$, $NO_2$ or $SR_7$.

Procedure 2: C-alkylation of heterocyclic compounds containing an acidic C—H moiety, i.e., activated by a carbonyl or sulfonyl group, by substrates of the Formula XI wherein M is Cl, Br, or iodine; or C-benzoylation with benzoyl chlorides of the Formula XI, wherein m=1, M is Cl, and G is Cl, Br, $CH_2Cl$, $CH_2Br$, $NO_2$ or $SR_7$.

Procedure 3: Reactions of derivatives of Formula XI, wherein M is $NH_2$, NHOH, or $NHNH_2$, as nucleophiles with bifunctional acrylic and cyclic reagents, which ultimately are converted to various Q values.

Procedure 4: Use of acid-derivatives of Formula XI, wherein M is $COOCH_3$, $COHNNH_2$, CN, or COCl; see Example 4.

Procedure 5: Synthesis from dianions derived from N-protected-(o-methyl aromatic sulfonamides) of Formula XI, wherein M is H, n=1, $R_8$=H, and G is $SO_2$NH-t-butyl or $SO_2NHSi(CH_3)_2$-t-butyl. These benzyl or benzyl-like dianions can be prepared by reaction of the appropriate sulfonamide, as defined above, with two equivalents of n-butyllithium at low temperatures in an inert solvent. In some instances, conversion of the lithium dianions to copper-lithium species is dictated by the literature and can be accomplished by known procedures.

Procedure 6: Reactions of acyclic anions with aldehydes of the Formula XI, wherein M is CHO (m=0). Further transformations, as described in the cited literature (Table 2) provide compounds of the Formula XII.

Procedure 7: Reactions of anions derived from aromatic heterocycles such as thiophene, furan, pyrrole, and pyridine (or simple substituted analogues) which act as "masked" heterocycles of the form Q. For example, alkylation reactions of such anions with compounds of the Formula XI, wherein M is Cl, Br, or iodine, provide intermediates which upon reduction (see for example conversions B and K in Table 1) yield compounds of the Formula XII.

Procedure 8: Synthesis of compounds of the Formula XII wherein M is a vinyl group (m=0): see reference 37.

Procedure 9: This procedure involves the use of compounds which are related to XI, but are outside the defined limits of XI. These compounds may be prepared by literature procedures from compounds of the Formula XI as defined. Additional functional group manipulation is then required, the procedures of which are described in the references cited in Table 2, to convert these compounds to compounds of the Formula XII.

Procedure 10: This procedure is the conversion of the Q value, contained in the Formula XII to a different Q value. These conversion procedures are summarized in Table 1. When applicable, the conversion procedures of Table 1 are cited by their letter designation in Table 2.

TABLE 1

CONVERSION PROCEDURES

| Designation | From | To | References |
|---|---|---|---|
| A | lactone | lactam | 1–3 |
| B | thiophene furan pyrrole | tetrahydro derivative | 4–6 |
| C | sulfide | sulfoxide or sulfone | 7 |
| D | lactone, lactam, sulfone or sultam | α-unsaturated derivative | 8, 84 |
| E | lactam | cyclic amine | 9–11 |
| F | cycloketone | lactone | 12–14 |
| G | dihydro-γ-pyrone | tetrahydro-γ-pyrone | 15–19 |
| H | dihydro-γ-pyridone | tetrahydro-γ-pyridone | 20–22 |
| I | γ-pyrone | γ-pyridone | 23–25 |
| J | lactone | tetrahydrofuran or tetrahydropyran | 26 |
| K | pyridine (including quaternary salts) | piperidine or N—substituted piperidines | 27–28 |
| L | anhydride | succinimide | |

Table 2 sumarizes selected synthetic procedures viable for the synthesis of compounds of Formula XII. Table 2 is not meant to be all inclusive, but does provide synthetic routes, which are well established and precedented in the literature, through the known chemical procedures (1–10), conversions (A–L), and methods described in the references (1–84) or slight modifications thereof.

For example, the preparation of a compound of Formula XII, where Q is $Q_1$ and $X_b$ is $NR_5$ can be carried out according to the procedure outlined in line number 2 Table 2. Thus alkylation (procedure 2) of butyrolactone (QH=Q-1 where $X_b$=0) with an appropriately substituted alkyl halide as described in references 29–31, followed by conversion of the lactone moiety to a lactam (conversion procedure A) provides the desired compound of Formula XII. Finally, compounds of Formula XII are converted to the desired sulfonylureas of Formula I via one or more of the procedures outlined in Equation 1 through 3.

TABLE 2

Preparative Schemes for Compounds of the Formula XII

| No. | Q | $X_b$ | $X_c$ | Proc.[1] | $QH(X_{b(c)})$[2] | Conv.[3] Proc. | Ref. | Comments |
|---|---|---|---|---|---|---|---|---|
| 1 | Q-1 | O | — | 2 | 1(O) | — | 29–31 | |
| 2 | Q-1 | $NR_5$ | — | 2 | 1(O) | A | 29–31 | |
| 3 | Q-1 | $NR_5$ | — | 2 | 1($NR_5$) | | 32–35 | |
| 4 | Q-2 | O | — | 5 | | | 36 | |
| 5 | Q-2 | $NR_5$ | — | 5 | | A | 36 | |
| 6 | Q-3 | O | — | 8 | | | 37 | |
| 7 | Q-3 | $NR_5$ | — | 8 | | A | 37 | |
| 8 | Q-4 | — | — | 1 | 4 | — | | See Example 1 |
| 9 | Q-5 | — | — | 2 | 5 | | 38,39 | |
| 10 | Q-6 | — | — | 5 | 18 | | 40–42 | 1,4-Addition |
| 11 | Q-7 | — | — | 2 | | | 43–45 38 | |

TABLE 2-continued
Preparative Schemes for Compounds of the Formula XII

| No. | Q | $X_b$ | $X_c$ | Proc.[1] | $QH(X_{b(c)})$[2] | Conv.[3] Proc. | Ref. | Comments |
|---|---|---|---|---|---|---|---|---|
| 12 | Q-8 | | | 9 | | | | Cyclize a halo-sulfonamide with base |
| 13 | Q-9 | | | 9 | — | | | Cyclize a halo-sulfonamide with base |
| 14 | Q-10 | — | — | 1 | — | | 46 | Analogous to Example 1 |
| 15 | Q-11 | | $NR_5$ | 2 | | | 49 | |
| 16 | Q-11 | | S | 2 | | | 38,50 | |
| 17 | Q-11 | | SO | 2 | | C | 38,50 | |
| 18 | Q-11 | | $SO_2$ | 2 | | C | 38,50 | |
| 19 | Q-11 | — | O | 6 | | | 51,52 | |
| 20 | Q-12 | — | $NR_5$ | 2 | | | 49 | |
| 21 | Q-12 | — | S | 9 | | | 53,54 | See also ref 50 |
| 22 | Q-12 | — | SO | 9 | | C | 53,54 | See also ref 50 |
| 23 | Q-12 | — | $SO_2$ | 9 | | C | 53,54 | See also ref 50 |
| 24 | Q-12 | — | O | 9 | | | 55 | |
| 25 | Q-13 | | O | 9 | | | 55 | |
| 26 | Q-13 | | S | 9 | | | 50, 52–54 | |
| 27 | Q-13 | | SO | 9 | | C | 50, 52–54 | |
| 28 | Q-13 | | $SO_2$ | 9 | | C | 50, 52–54 | |
| 29 | Q-13 | | $NR_5$ | 5 | | | | In addition to to appropriate pyrrolidinone See also ref. 56 |
| 30 | Q-14 | — | — | 1 | | | | Protection of co may be necessary |
| 31 | Q-15 | O | — | 5 | | D | 36 | |
| 32 | Q-15 | $NR_5$ | —. | 5 | | D,A | 36 | Conversion D then A |
| 33 | G-16 | O | | 8 | | D | 37 | |
| 34 | Q-16 | | $NR_5$ | | 8 | D,A | 37 | Conversion D then A |
| 35 | Q-17 | — | — | 1 | 4 | D | | See example 1 |
| 36 | Q-17 | — | — | 1 | 17 | | | See example 1 |
| 37 | Q-18 | — | — | 5 | 20 | D | 58–60 | 1,4 Addition to QH-18 followed by in situ conversion D |
| 38 | Q-19 | — | — | 1 | | | | Use α, β unsaturated propane sultam |
| 39 | Q-20 | O | | 2 | | | 29–31 | |
| 40 | Q-20 | $NR_5$ | | 2 | | | 32–35 | See ref 35. R = H |
| 41 | Q-21 | O | | 9 | | | 57 | Ref 57 discusses lactonization of hydroxy-acids |
| 42 | Q-21 | $NR_5$ | | 9 | | D | 57 | |
| 43 | Q-22 | O | | 9 | | | 57 | |
| 44 | Q-22 | $NR_5$ | | 9 | | A | 57 | |
| 45 | Q-23 | O | | 2 | 5 | F | 38,39 | |
| 46 | Q-23 | — | — | 2 | 5 | F,A | | Procedure E then A |
| 47 | Q-24 | — | — | 1 | 24 | | | Modification of example 1 |
| 48 | Q-25 | — | — | 2 | 25 | | 37,39 | |
| 49 | Q-26 | | | 5 | | | 40–42 | 1,4 Addition |
| 50 | Q-26 | —. | — | 9 | | | | Cyclization of halo-sulfonamides with base |
| 51 | Q-27 | — | — | 2 | 27 | | 43–45 | |
| 52 | Q-28 | — | — | 1 | | | | Modification of Example 1 |
| 53 | Q-29 | | $NR_5$ | 2 | $29(NR_5)$ | | 49 | |
| 54 | Q-29 | | S | 2,9 | | | 53,54, 58 | |
| 55 | Q-29 | | SO | 2,9 | | C | 38,53, 54 | |
| 56 | Q-29 | | $SO_2$ | 2,9 | | C | 38,53 | |

TABLE 2-continued
Preparative Schemes for Compounds of the Formula XII

| No. | Q | $X_b$ | $X_c$ | Proc.[1] | $QH(X_{b(c)})$[2] | Conv.[3] Proc. | Ref. | Comments |
|---|---|---|---|---|---|---|---|---|
| 57 | Q-29 |  | O | 2,9 |  |  | 54 |  |
| 58 | Q-30 | — | O | 5 | 41(O) |  | 38 | 1,4 Addition |
| 59 | Q-30 | — | NR$_5$ | 5 | 41(NR$_5$) |  | 40-42 | 1,4 Addition |
| 60 | Q-30 | — | S | 5 | 41(S) |  | 40-42 | 1,4 Addition |
| 61 | Q-30 | — | SO | 5 | 41(S) | C | 40-42 | 1,4 Addition |
| 62 | Q-30 | — | SO$_2$ | 5 | 41(S) | C | 40-42 | 1,4 Addition |
| 63 | Q-31 | — | S | 9 | — |  | 53-54 |  |
| 64 | Q-31 | — | SO | 9 | — | C | 53-54 |  |
| 65 | Q-31 | — | SO$_2$ | 9 | — | C | 53-54 |  |
| 66 | Q-31 | — | O | 9 | — | → | — |  |
| 67 | Q-31 | — | NR$_5$ | 9 | — | — | — |  |
| 68 | Q-32 | — | NR$_5$ | 2 | — | — | 49 |  |
| 69 | Q-32 | — | O | 2 |  |  | 38 | Modification of ref. 49 |
| 70 | Q-32 | — | S | 2 |  |  | 38 | Modification of ref. 49 |
| 71 | Q-32 | — | SO | 2 |  |  | 38 | Modification of ref. 49 |
| 72 | Q-32 | — | SO$_2$ | 2 |  |  | 38 | Modification of ref. 49 |
| 73 | Q-33 |  |  | 1 | 33 |  |  | C=O protection may be necessary |
| 74 | Q-34 |  | O | 2 | 34(O) |  | 38 |  |
| 75 | Q-34 |  | S | 2 | 34(S) |  | 38 |  |
| 76 | Q-34 |  | SO | 2 | 34(S) | C | 38 |  |
| 77 | Q-34 |  | SO$_2$ | 2 | 34(S) | C | 38 |  |
| 78 | Q-34 |  | NR$_5$ | 2 | 34(NR$_5$) |  | 38 |  |
| 79 | Q-35 |  | O | 4 |  | G | 59 |  |
| 80 | Q-35 |  | NR$_5$ | 9 |  | H | 61 |  |
| 81 | Q-35 |  | S | 9 |  |  | 62 |  |
| 82 | Q-35 |  | SO | 9 |  | C | 62 |  |
| 83 | Q-35 |  | SO$_2$ | 9 |  | C | 62 |  |
| 84 | Q-36 |  |  | 1 | 36 |  |  | C=O protection may be necessary |
| 85 | Q-37 | O |  | 2 | 5 | F,D | 38,39 |  |
| 86 | Q-37 | NR$_5$ |  | 2 | 5 | F,D,A | 38,39 |  |
| 87 | Q-38 | — | — | 2 | 38 |  |  | Modification of Example 1 |
| 88 | Q-39 | — | — | 2 | 25 | D | 38,39 |  |
| 89 | Q-39 | — | — | 2 | 39 |  | 38 |  |
| 90 | Q-40 | — | — | 1 |  |  |  | Modification of Example 1 |
| 91 | Q-41 |  | NR$_5$ | 2 | 30(NR$_5$) | D | 49 |  |
| 92 | Q-41 |  | O |  |  | D | 38 |  |
| 93 | Q-41 |  | S |  |  | D | 38 |  |
| 94 | Q-41 |  | SO |  |  | D,C | 38 |  |
| 95 | Q-41 |  | SO$_2$ |  |  | D,C | 38 |  |
| 96 | Q-42 |  | S | 9 |  | D | 62 |  |
| 97 | Q-42 |  | NR$_5$ | 9 |  |  | 61 |  |
| 98 | Q-42 |  | SO | 9 |  | D,C | 62 |  |
| 99 | Q-42 |  | SO$_2$ | 9 |  | D,C | 6 |  |
| 100 | Q-42 | — | O | 2 |  |  | 38 |  |
| 101 | Q-43 | — | — | 1 | 35 | D |  |  |
| 102 | Q-44 | O | — | 9 |  |  | 63-65 |  |
| 103 | Q-44 | NR$_5$ | — | 9 |  |  | 63-65 |  |
| 104 | Q-45 |  |  | 3 |  |  |  | Reaction of amine with γ-pyrone |
| 105 | Q-46 |  |  | 4 |  |  | 66 |  |
| 106 | Q-47 |  |  | 4 |  |  | 67-69 | Ref 69 contains N—alkylation procedures |
| 107 | Q-48 |  |  | 4 |  |  | 70 |  |
| 108 | Q-49 |  |  | 4 |  |  | 71 |  |
| 109 | Q-50 |  |  | 4 |  |  | 72-73 |  |
| 110 | Q-51 |  |  | 4 |  |  | 74 |  |
| 111 | Q-52 |  |  | 4 |  |  | 75-77 |  |
| 112 | Q-53 |  |  | 4 |  |  | 78 |  |
| 113 | Q-54 |  |  | 1 | 54 |  | 79,80 |  |
| 114 | Q-55 |  |  | 1 | 55 |  | 81 |  |
| 115 | Q-56 |  |  | 1 | 56 |  |  |  |
| 116 | Q-57 |  |  | 9 |  |  | 82 |  |
| 117 | Q-58 |  |  | 8 |  |  | 83 |  |
| 118 | Q-59 |  |  | 1 | 59 |  |  |  |
| 119 | Q-60 |  |  | 1 | 60 |  |  |  |
| 120 | Q-61 |  |  | 9 |  |  |  |  |

TABLE 2-continued

Preparative Schemes for Compounds of the Formula XII

| No. | Q | $X_b$ | $X_c$ | Proc.[1] | $QH(X_{b(c)})$[2] | Conv.[3] Proc. | Ref. | Comments |
|---|---|---|---|---|---|---|---|---|
| 121 | Q-62 | | | 1 | 62 | | | |
| 122 | Q-63 | | | 3 | | | | M = NHOH |
| 123 | Q-64 | | | 2 | 64 | | 38 | $R_5$ = 16 |
| 124 | Q-65 | | | 1 | 65 | | | |
| 125 | Q-66 | | | 2 | 66 | | 38 | |
| 126 | Q-67 | | | 1 | 67 | | | |
| 127 | Q-68 | | | 2 | 68 | | 38 | |
| 128 | Q-69 | | | 1 | 69 | | | |
| 129 | Q-69 | | | 3 | | | | M = NHOH |
| 130 | Q-70 | | | 2 | 70 | | 38 | |
| 131 | Q-71 | | | 9 | | | | |
| 132 | Q-72 | | | 1 | 72 | | | |
| 133 | Q-73 | | | 1 | 73 | | | |
| 134 | Q-74 | | | 1 | 74 | | | |
| 135 | Q-75 | | | 6 | L | | | |
| 136 | Q-76 | | | 1 | 76 | | | |
| 137 | Q-77 | | | 6 | L,D | | | |
| 138 | Q-78 | | | 6 | | | | Anion from $CH_3CO_2CH_2CH_2$—$CO_2CH_3$ then ring close with acid |
| 139 | Q-79 | | | 1 | 79 | | | |
| 140 | Q-80 | | | 1 | 80 | | | |
| 141 | Q-81 | | | 2 | 81 | | 38 | |
| 142 | Q-82 | | | 1 | 82 | | | |
| 143 | Q-83 | | | 1 | 83 | | | |
| 144 | Q-84 | | | 1 | 84 | | | |
| 145 | Q-85 | | | 2 | 85 | | 38 | |
| 146 | Q-86 | | | 2 | 86 | | 38 | |
| 147 | Q-87 | | | 2 | 87 | | 38 | |

[1]procedures of 1-10
[2]for example when $QH(X_b)$ = 1(O); QH is $Q_1$, and $X_b$ is oxygen which suggests butyrolactone would be a viable starting material
[3]conversion procedures (A-L) are described in Table I.

The preparation of the compounds of this invention is further illustrated by the following specific examples.

EXAMPLE 1

1-[(2-(Phenylmethylthio)phenylmethyl]-2-pyrrolidinone

To a solution of 1.35 g of potassium-tert-butoxide in 25 mL of dimethylformamide, cooled to 0° C., was added 0.92 mL of 2-pyrrolidinone. As a white precipitate formed, the mixture was stirred for 10 minutes, and 3.0 g of 2-phenylmethylthio chloromethyl benzene was added in one portion. The resulting solution was allowed to warm to room temperature, stirred for 1 hour, poured into water, and extracted with methylene chloride. The organic layer was washed well with water, dried over magnesium sulfate, filtered, and the filtrate evaporated to leave 3.0 g of a yellow oil.

| NMR (CDCl₃) ppm: | 7.3 | (m, 9H, ArH) |
|---|---|---|
| | 4.5 | (s, 2H, CH₂) |
| | 4.0 | (s, 2H CH₂) |
| | 3.05 | (t, 2H, —CH₂—) |
| | 2.3 | (t, 2H, —CH₂—) |
| | 1.7–2.05 | (m, 2H, CH₂) |

EXAMPLE 2

2-(2-Oxo-1-pyrrolidinylmethyl)benzenesulfonamide

To a solution of 2.6 g of the compound of Example 1 dissolved in 100 mL of acetic acid, containing 0.5 mL of water, and cooled to 15° C., was bubbled in chlorine gas for 15 minutes. A slight exotherm of 5° C. was noted. The reaction was stirred for an additional 5 minutes, poured into ice water, and extracted with methylene chloride. The organic layer was washed with saturated sodium bicarbonate, dried over magnesium sulfate, filtered, and evaporated to an oil. The oil was immediately dissolved in 100 mL of tetrahydrofuran and treated with 2 mL of concentrated ammonium hydroxide and stirred for 1 hour. The tetrahydrofuran was removed on the rotaryevaporator to give a semisolid. The residue was then triturated with water to form a sticky solid which was filtered off and triturated with ether to provide 1.1 g of an off-white solid; m.p. 149°–151° C. IR (Nujol) 1660(C=O) cm⁻¹.

EXAMPLE 3

N-[((4,6-dimethoxypyrimidin-2-yl)aminocarbonyl)-2-(2-oxo-1-pyrrolidinylmethyl]-benzenesulfonamide To a suspension of 254 mg of the product of Example 2 in 10 mL of acetonitrile, containing 275 mg of phenyl(4,6-dimethoxypyrimidin-2-yl)carbamate, was added 0.15 mL of 1,8-diazabicyclo[5.4.0]undec-7-ene (DBU). The resultant solution was stirred for 2 hours, diluted with 20 mL of water and acidified with 5 drops of concentrated hydrochloric acid. n-Butylchloride (10 mL) was added, stirred, and the white precipitate was filtered. The collected white solid was washed with a little water, suction dried and finally dried in vacuo @ 70° C. overnight to afford 200 mg of a white solid, m.p. 185°–187° C.

| IR (Nujol) | 1730 (C = O) | | |
|---|---|---|---|
| | 1668 (C = O) | cm⁻¹; | |
| NMR (CDCl₃) | ppm | 12.76 | (bs,1H, NH) |
| | | 8.21 | (m, 1H, ArH) |
| | | 7.36–7.7 | (m, 3H, ArH) |

| | |
|---|---|
| 7.22 | (bs, 1H, NH) |
| 5.80 | (s, 1H, PyH) |
| 5.01 | (s, 2H, CH$_2$) |
| 3.96 | (s, 6H, OCH$_3$) |
| 3.32 | (t, 2H, CH$_2$) |
| 2.46 | (t, 2H, CH$_2$) |
| 2.03 | (m, 2H, CH$_2$) |

USE OF TABLES A, J, AND Q

For purposes of expediency and avoidance of voluminous pages of tables each sulfonylurea is divided into three structural pieces as illustrated below.

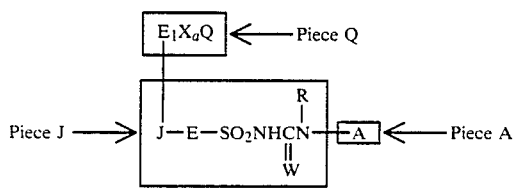

Each structural piece A, J, and Q is fully defined separately in Tables A, J and Q respectively and requires the designation of a particular structure from one of the structure(s) assigned to each of these tables. Thus to fully delineate a complete structure for a unique sulfonylurea it requires the information from one entry in each of the tables A, J, and Q and a designation of one of the structures assigned to that table. Note that only one structure, namely structure A, is assigned to Table A and need not be specifically designated.

The use of Tables A, J, and Q provides an alternative to listing individual compounds line by line as is done in a conventional table. It is the applicant's intent to specifically disclose each and every compound that can be constructed from Tables A, J and Q using the procedure described above and illustrated below.

The use of Tables A, J, and Q can be illustrated by the following. For example, specifically claimed is compound of Formula XIII and is

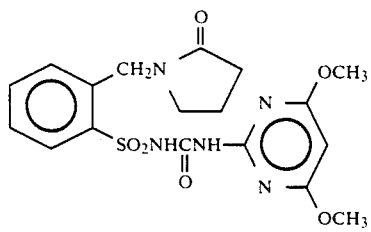

XIII listed in Tables A, J, and Q as entry number 4 of Table A; entry number one of Table J—Structure B; and entry number seven of Table Q—Structure J. As a shorthand notation, compound of Formula XIII can be listed in a matrix form as:

4; 1-B; 7-J

This provides a convenient method for listing the melting point of compounds as is done in the melting point table (AJQ) (see line number one of Table AJQ). Each compound for which a melting point is available is simply listed in the melting point table (AJQ) as the entry number of Table A; entry number-structure for Table J; and entry number-structure for Table Q in that order.

Also specifically claimed is compound of formula XIV shown below.

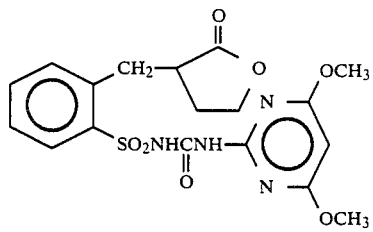

XIV

Compound of Formula XIV is found in Tables A, J, and Q as entry number four of Table A; entry number one of Table J-Structure B; and entry number one of Table Q-Structure J or in the convenient matrix form as:

4; 1-B; 1-J

By analogy compounds of Formula XV and XVI having structures as shown below

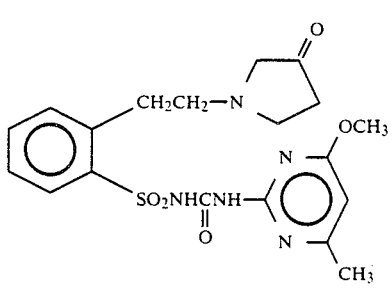

XV

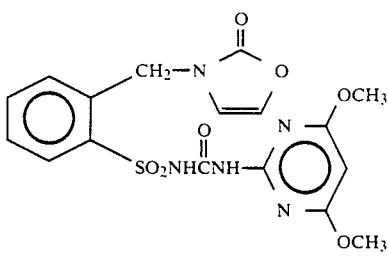

XVI have matrix designations of 2; 1-B; 19-L and 4; 1-B; 76-J respectively.

The structures assigned to Tables A, J, and Q are shown below followed by Tables A, J, and Q and finally the melting point Table AJQ.

STRUCTURE FOR TABLE A

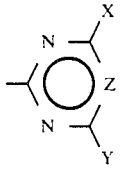

A

STRUCTURES FOR TABLE J

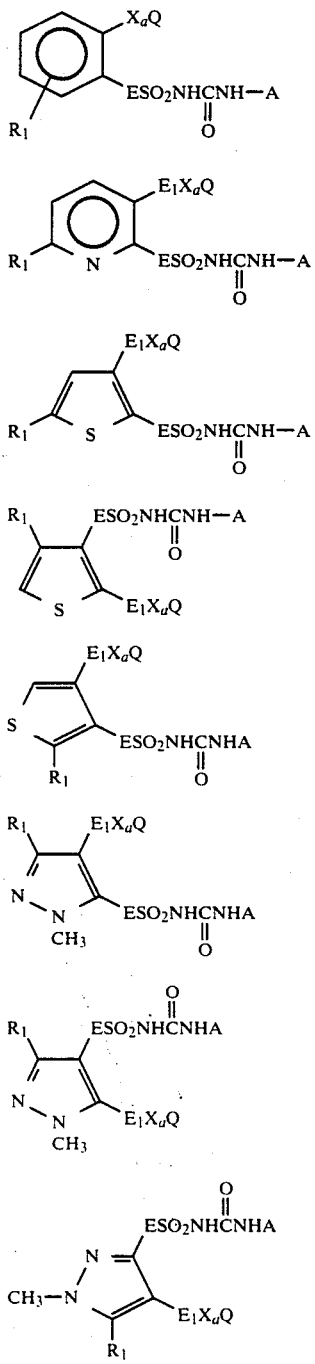

STRUCTURES FOR TABLE Q

—CH₂Q  A $\underset{|}{\overset{CH_3}{-CH-Q}}$  B

—CH₂CH₂—Q  C $\underset{\overset{\|}{O}}{-C}-Q$  D

SCH₂Q  N $\underset{\overset{\|}{O}}{SCH_2Q}$  O

SO₂CH₂Q  P

OCH₂Q  Q

TABLE A FOR STRUCTURE A

| Entry | X | Y | Z |
|---|---|---|---|
| 1 | CH₃ | CH₃ | CH |
| 2 | CH₃ | OCH₃ | CH |
| 3 | CH₃ | OCH₃ | N |
| 4 | OCH₃ | OCH₃ | CH |
| 5 | OCH₃ | OCH₃ | N |
| 6 | Cl | OCH₃ | CH |
| 7 | CH₃ | C₂H₅ | CH |
| 8 | CH₃ | CH₂OCH₃ | CH |
| 9 | CH₃ | CH₂OCH₃ | N |
| 10 | CH₃ | NHCH₃ | CH |
| 11 | CH₃ | NHCH₃ | N |
| 12 | CH₃ | CH(OCH₃)₂ | CH |
| 13 | CH₃ | CH(OCH₃)₂ | N |
| 14 | CH₃ | Cyclopropyl | CH |
| 15 | CH₃ | Cyclopropyl | N |
| 16 | OCH₃ | C₂H₅ | CH |
| 17 | OCH₃ | C₂H₅ | N |
| 18 | OCH₃ | CH₂OCH₃ | CH |
| 19 | OCH₃ | CH₂OCH₃ | N |
| 20 | OCH₃ | NHCH₃ | CH |
| 21 | OCH₃ | NHCH₃ | N |
| 22 | OCH₃ | CH(OCH₃)₂ | CH |
| 23 | OCH₃ | CH(OCH₃)₂ | N |
| 24 | OCH₃ | Cyclopropyl | CH |
| 25 | OCH₃ | Cyclopropyl | N |
| 26 | OCH₂CH₃ | CH₃ | CH |
| 27 | OCH₂CH₃ | CH₃ | N |
| 28 | OCH₂CH₃ | OCH₃ | CH |
| 29 | OCH₂CH₃ | OCH₃ | N |
| 30 | OCH₂CH₃ | CH₂OCH₃ | CH |
| 31 | OCH₂CH₃ | CH₂OCH₃ | N |
| 32 | OCH₂CH₃ | NHCH₃ | CH |
| 33 | OCH₂CH₃ | NHCH₃ | N |
| 34 | OCH₂CH₃ | CH(OCH₃)₂ | CH |
| 35 | OCH₂CH₃ | CH(OCH₃)₂ | N |
| 36 | Cl | OCF₂H | CH |
| 37 | OCF₂H | CH₃ | CH |
| 38 | OCF₂H | OCH₃ | CH |
| 39 | OCF₂H | C₂H₅ | CH |
| 40 | OCF₂H | CH₂OCH₃ | CH |
| 41 | OCF₂H | NHCH₃ | CH |
| 42 | OCF₂H | CH(OCH₃)₂ | CH |
| 43 | OCF₂H | Cyclopropyl | CH |

TABLE J FOR STRUCTURES B-1[(a)]

| Entry | E | R₁ No. refers to position in Structure B only |
|---|---|---|
| 1 | — (Single bond) | H |
| 2 | — | 5-CH₃ |
| 3 | — | 5-CH₂Cl |
| 4 | — | 5-OCH₃ |
| 5 | — | 5-SCH₃ |
| 6 | — | 5-SCH₂CH₃ |
| 7 | — | 5-Cl |
| 8 | — | 6-F |
| 9 | — | 5-NO₂ |
| 10 | — | 6-SO₂N(CH₃)₂ |
| 11 | — | 5-SOCH₃ |
| 12 | — | 3-Cl |
| 13 | — | 6-SO₂CH₃ |
| 14 | — | 5-CH₂CN |
| 15 | — | 5-CN |

TABLE J FOR STRUCTURES B-I[a]

| Entry | E | $R_1$ No. refers to position in Structure B only |
|---|---|---|
| 16 | — | 6-CN |
| 17 | — | 5-CO$_2$CH$_3$ |
| 18 | — | 5-CF$_3$ |
| 19 | CH$_2$ | H |
| 20 | CH$_2$ | 5-CN |
| 21 | CH$_2$ | 5-SCH$_3$ |
| 22 | CH$_2$ | 5-OCH$_3$ |
| 23 | CH$_2$ | 5-Cl |
| 24 | O | H |
| 25 | O | 5-SCH$_3$ |

[a] W = O, R = H

TABLE Q FOR STRUCTURES J-Q

| Entry | Q | $x_b$ | $x_c$ | $R_5$ | $R_6$ | Proviso (See end of Table) |
|---|---|---|---|---|---|---|
| 1 | Q-1 | O | — | — | — | a |
| 2 | Q-1 | NR$_5$ | — | CH$_3$ | — | — |
| 3 | Q-2 | O | — | — | — | — |
| 4 | Q-2 | NR$_5$ | — | CH$_3$ | — | — |
| 5 | Q-3 | O | — | — | — | — |
| 6 | Q-3 | NR$_5$ | — | CH$_3$ | — | — |
| 7 | Q-4 | — | — | — | — | — |
| 8 | Q-5 | — | — | — | — | — |
| 9 | Q-6 | — | — | — | — | — |
| 10 | Q-7 | — | — | CH$_3$ | — | — |
| 11 | Q-8 | — | — | CH$_3$ | — | — |
| 12 | Q-9 | — | — | CH$_3$ | — | — |
| 13 | Q-10 | — | — | — | — | — |
| 14 | Q-11 | — | O | — | — | — |
| 15 | Q-11 | — | NR$_5$ | CH$_2$CH$_3$ | — | — |
| 16 | Q-12 | — | NR$_5$ | CH$_2$CH$_3$ | — | — |
| 17 | Q-12 | — | O | — | — | — |
| 18 | Q-13 | — | O | — | — | — |
| 19 | Q-14 | — | — | — | — | — |
| 20 | Q-15 | O | — | — | — | — |
| 21 | Q-15 | NR$_5$ | — | CH$_3$ | — | — |
| 22 | Q-16 | O | — | — | — | b |
| 23 | Q-16 | NR$_5$ | — | CH$_3$ | — | b |
| 24 | Q-17 | — | — | — | — | — |
| 25 | Q-18 | — | — | — | — | — |
| 26 | Q-19 | — | — | — | — | — |
| 27 | Q-20 | O | — | — | — | — |
| 28 | Q-20 | NR$_5$ | — | CH$_3$ | — | — |
| 29 | Q-21 | O | — | — | — | — |
| 30 | Q-22 | O | — | — | — | — |
| 31 | Q-23 | O | — | — | — | — |
| 32 | Q-23 | NR$_5$ | — | CH$_3$ | — | — |
| 33 | Q-24 | — | — | — | — | — |
| 34 | Q-25 | — | — | — | — | — |
| 35 | Q-26 | — | — | CH$_3$ | — | — |
| 36 | Q-27 | — | — | CH$_3$ | — | — |
| 37 | Q-28 | — | — | — | — | — |
| 38 | Q-29 | — | NR$_5$ | CH$_3$ | — | — |
| 39 | Q-30 | — | O | — | — | — |
| 40 | Q-31 | — | O | — | — | — |
| 41 | Q-32 | — | NR$_5$ | CH$_3$ | — | — |
| 42 | Q-33 | — | — | — | — | — |
| 43 | Q-33 | — | O | — | — | — |
| 44 | Q-34 | — | NR$_5$ | CH$_3$ | — | — |
| 45 | Q-35 | — | O | — | — | — |
| 46 | Q-36 | — | — | — | — | — |
| 47 | Q-37 | O | — | — | — | b |
| 48 | Q-38 | NR$_5$ | — | CH$_3$ | — | — |
| 49 | Q-38 | — | — | — | — | — |
| 50 | Q-39 | — | — | — | — | — |
| 51 | Q-40 | — | — | — | — | — |
| 52 | Q-41 | — | NR$_5$ | CH$_3$ | — | b |
| 53 | Q-41 | — | O | — | — | b |
| 54 | Q-42 | — | O | — | — | b |
| 55 | Q-42 | — | NR$_5$ | — | — | b |
| 56 | Q-43 | — | — | — | — | — |
| 57 | Q-44 | — | O | — | — | b |
| 58 | Q-44 | — | NR$_5$ | CH$_3$ | — | b |
| 59 | Q-45 | — | — | — | — | b |
| 60 | Q-46 | — | — | CH$_3$ | — | b |
| 61 | Q-46 | — | — | H | — | b |
| 62 | Q-47 | — | — | CH$_3$ | — | b |
| 63 | Q-48 | — | — | CH$_3$ | — | b |
| 64 | Q-49 | — | — | CH$_3$ | — | b |
| 65 | Q-50 | — | — | CH$_3$ | CH$_3$ | b |
| 66 | Q-51 | — | — | — | — | b |
| 67 | Q-52 | — | — | — | — | b |
| 68 | Q-53 | — | — | — | CH$_3$ | b |
| 69 | Q-54 | — | — | — | — | — |
| 70 | Q-54 | — | — | — | — | a |
| 71 | Q-55 | — | — | — | — | a |
| 72 | Q-56 | — | — | — | — | — |
| 73 | Q-57 | — | — | CH$_3$ | — | — |
| 74 | Q-58 | — | — | H | — | — |
| 75 | Q-58 | — | — | CH$_3$ | — | — |
| 76 | Q-59 | — | — | — | — | — |
| 77 | Q-60 | — | — | CH$_3$ | — | — |
| 78 | Q-61 | — | — | CH$_3$ | CH$_3$ | — |
| 79 | Q-62 | — | — | CH$_3$ | — | — |
| 80 | Q-63 | — | — | — | — | — |
| 81 | Q-63 | — | — | — | — | c |
| 82 | Q-64 | — | — | CH$_3$ | — | — |
| 83 | Q-65 | — | — | — | — | — |
| 84 | Q-66 | — | — | CH$_3$ | — | — |
| 85 | Q-67 | — | — | — | — | — |
| 86 | Q-68 | — | — | CH$_3$ | — | — |
| 87 | Q-69 | — | — | — | — | — |
| 88 | Q-70 | — | — | CH$_3$ | — | — |
| 89 | Q-71 | — | — | — | — | — |
| 90 | Q-72 | — | — | CH$_3$ | — | — |
| 91 | Q-73 | — | — | CH$_3$ | — | — |
| 92 | Q-74 | — | — | — | — | — |
| 93 | Q-75 | — | — | CH$_3$ | — | — |
| 94 | Q-76 | — | — | — | — | — |
| 95 | Q-77 | — | — | CH$_3$ | — | b |
| 96 | Q-78 | — | — | — | — | — |
| 97 | Q-79 | — | — | — | — | — |
| 98 | Q-80 | — | — | — | — | — |
| 99 | Q-81 | — | — | CH$_3$ | — | — |
| 100 | Q-82 | — | — | — | — | — |
| 101 | Q-83 | — | — | — | — | — |
| 102 | Q-84 | — | — | CH$_3$ | — | — |
| 103 | Q-85 | — | — | — | — | — |
| 104 | Q-86 | — | — | — | — | — |
| 105 | Q-87 | — | — | — | — | — |

[a] Q$_1$ is substituted by a 4-methyl group
[b] Structure B of Table J is excluded with the use of the Q value designated in this entry
[c] Substituted by α,α-dimethyl

MELTING POINT TABLE (AJQ)

| DESIGNATIONS: No. | TABLE A: ENTRY #: Matrix Designation | TABLE J: ENTRY # - STRUCTURE | TABLE Q ENTRY # - STRUCTURE | MP° C. |
|---|---|---|---|---|
| 1 | 4: | 1-B: | 7-J | 185–87 |
| 2 | 5: | 1-B: | 7-J | 194–95 |
| 3 | 1: | 1-B: | 72-J | 184–85 |
| 4 | 4: | 1-B: | 72-J | 139–42 |
| 5 | 5: | 1-B: | 72-J | 184–85 |
| 6 | 1: | 1-B: | 70-J | 192–94 |
| 7 | 2: | 1-B: | 70-J | 177–78 |
| 8 | 4: | 1-B: | 70-J | 183–85 |
| 9 | 6: | 1-B: | 70-J | 202–04 |
| 10 | 3: | 1-B: | 70-J | 185–86 |
| 11 | 5: | 1-B: | 70-J | 195–96 |
| 12 | 2: | 1-B: | 1-J | 202–04.5 |
| 13 | 6: | 1-B: | 1-J | 178–82.5 |
| 14 | 1: | 1-B: | 1-J | 193–96 |
| 15 | 5: | 1-B: | 1-J | 182–85 |
| 16 | 3: | 1-B: | 1-J | 188–94 |
| 17 | 4: | 1-B: | 1-J | 178–82 |

-continued

| | | |
|---|---|---|
| 18 | 1: 1-E: 7-J | 174–76 |
| 19 | 2: 1-E: 7-J | 163–65 |
| 20 | 4: 1-E: 7-J | 137–39 |
| 21 | 6: 1-E: 7-J | 182–83 |
| 22 | 3: 1-E: 7-J | 171–72 |
| 23 | 5: 1-E: 7-J | 169–71 |
| 24 | 1: 1-E: 72-J | 159–61 |
| 25 | 2: 1-E: 72-J | 146–55 |
| 26 | 4: 1-E: 72-J | 157–60 |
| 27 | 6: 1-E: 72-J | 146–50 |
| 28 | 3: 1-E: 72-J | 155–61 |
| 29 | 1: 1-E: 70-J | 190–91 |
| 30 | 2: 1-E: 70-J | 169–72 |
| 31 | 4: 1-E: 70-J | 129–31 |
| 32 | 6: 1-E: 70-J | 168–75 |
| 33 | 3: 1-E: 70-J | 154–59 |
| 34 | 5: 1-E: 70-J | 170–73 |
| 35 | 4: 1-E: 33-J | 150–60 |
| 36 | 5: 1-E: 33-J | 170–72 |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following proportions:

| | Weight Percent* | | |
|---|---|---|---|
| | Active Ingredient | Diluent(s) | Surfactant(s) |
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing corp., Ridgewood, New Jersey, as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering,* Dec. 4, 1967, pp. 147ff, and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 4

| Wettable Powder | |
|---|---|
| N—[[(4,6-dimethoxypyrimidin-2-yl)aminocarbonyl]-2-(2-oxo-1-pyrrolidinylmethyl)benzenesulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 5

| Wettable Powder | |
|---|---|
| N—[[4-methoxy-6-methyl-1,3,5-triazin-2-yl)-aminocarbonyl]-2-(2-oxo-1-pyrrolidinylmethyl)-benzenesulfonamide | 50% |
| sodium alkylnaphthalenesulfonate | 2% |
| low viscosity methyl cellulose | 2% |
| diatomaceous earth | 46% |

The ingredients are blended, coarsely hammermilled and then air-milled to produce particles essentially all below 10 microns in diameter. The product is reblended before packaging.

EXAMPLE 6

| Granule | |
|---|---|
| Wettable Powder of Example 5 | 5% |
| attapulgite granules (U.S.S. 20–40 mesh; 0.84–0.42 mm) | 95% |

A slurry of wettable powder containing 25% solids is sprayed on the surface of attapulgite granules while tumbling in a double-cone blender. The granules are dried and packaged.

EXAMPLE 7

| Extruded Pellet | |
|---|---|
| N—[[(4,6-dimethoxypyrimidin-2-yl)aminocarbonyl]-2-(2-oxo-1-pyrrolidinylmethyl)benzenesulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 8

| Oil Suspension | |
|---|---|
| N—[[(4-methoxy-6-methyl-1,3,5-triazin-2-yl)aminocarbonyl]-2-(2-oxo-1-pyrrolidinylmethyl)benzenesulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 9

| Wettable Powder | |
|---|---|
| N—[[(4-methoxy-6-methyl-1,3,5-triazin-2-yl)aminocarbonyl]-2-(2-oxo-1-pyrrolidinylmethyl)-benzenesulfonamide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 10

| Low Strength Granule | |
|---|---|
| N—[[(4,6-dimethoxypyrimidin-2-yl)aminocarbonyl]-2-(2-oxo-1-pyrrolidinylmethyl)benzenesulfonamide | 1% |
| N,N—dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 11

| Aqueous Suspension | |
|---|---|
| N—[[(4-methoxy-6-methyl-1,3,5-triazin-2-yl)aminocarbonyl]-2-(2-oxo-1-pyrrolidinylmethyl)benzenesulfonamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1% |
| water | 56.7% |

The ingredients are blended and ground together in a sand mill to produce particles essentially all under 5 microns in size.

EXAMPLE 12

| Solution | |
|---|---|
| N—[[(4,6-dimethoxypyrimidin-2-yl)aminocarbonyl]-2-(2-oxo-1-pyrrolidinylmethyl)benzenesulfonamide, sodium salt | 5% |
| water | 95% |

The salt is added directly to the water with stirring to produce the solution, which may then be packaged for use.

EXAMPLE 13

| Low Strength Granule | |
|---|---|
| N—[[(4-methoxy-6-methyl-1,3,5-triazin-2-yl)aminocarbonyl]-2-(2-oxo-1-pyrrolidinylmethyl)benzenesulfonamide | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 14

| Granule | |
|---|---|
| N—[[(4,6-dimethoxypyrimidin-2-yl)aminocarbonyl]-2-(2-oxo-1-pyrrolidinylmethyl)benezenesulfonamide | 80% |
| wetting agent | 1% |
| crude ligninsulfonate salt (containing | 10% |

| Granule | |
|---|---|
| 5-20% of the natural sugars) | |
| attapulgite clay | 9% |

The ingredients are blended and milled to pass through a 100 mesh screen. This material is then added to a fluid bed granular, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 15

| High Strength Concentrate | |
|---|---|
| N—[[(4,6-dimethoxypyrimidin-2-yl)aminocarbonyl]-2-(2-oxo-1-pyrrolidinylmethyl)benzenesulfonamide. | 99% |
| silica aerogel | 0.5% |
| synthetic amorphous silica | 0.5% |

The ingredients are blended and ground in a hammer-mill to produce a material essentially all passing a U.S. Ser. No. 50 screen (0.3 mm opening). The concentrate may be formulated further if necessary.

EXAMPLE 16

| Wettable powder | |
|---|---|
| N—[[(4,6-dimethoxypyrimidin-2-yl)aminocarbonyl]-2-(2-oxo-1-pyrrolidinylmethyl)benzenesulfonamide | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S. Ser. No. 50 screen and then packaged.

EXAMPLE 17

| Wettable Powder | |
|---|---|
| N—[[(4-methoxy-6-methyl-1,3,5-triazin-2-yl)aminocarbonyl]-2-(2-oxo-1-pyrrolidinylmethyl)-benzenesulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 18

| Oil Suspension | |
|---|---|
| N—[[(4,6-dimethoxypyrimidin-2-yl)aminocarbonyl]-2-(2-oxo-1-pyrrolidinylmethyl)benzenesulfonamide. | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 19

| Dust | |
|---|---|
| N—[[(4-methoxy-6-methyl-1,3,4-triazin-2-yl)aminocarbonyl]-2-(2-oxo-1-pyrrolidinylmethyl)-benzenesulfonamide | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

Utility

Test results indicate that the compounds of the present invention are highly active preemergent or postemergent herbicides or plant growth regulators. Many of them have utility for broad-spectrum pre and/or post-emergence weed control in areas where complete control of all vegetation is desired, such as around fuel storage tanks, ammunition depots, industrial storage areas, parking lots, drive-in theaters, around billboards, highway and railroad structures. Some of the compounds have utility for selective weed control in crops such as wheat, second barley. Alternatively, the subject compounds are useful to modify plant growth.

The rates of application for the compounds of the invention are determined by a number of factors, including their use as plant growth modifiers or as herbicides, the crop species involved, the types of weeds to be controlled, weather and climate, formulations selected, mode of application, amount of foliage present, etc. In general terms, the subject compounds should be applied at levels of around 0.005 to 10 kg/ha, the lower raters being suggested for use on lighter soils and/or those having a low organic matter content, for plant growth modification or for situations where only short-term persistence is required.

The compounds of the invention may be used in combination with any other commercial herbicides, examples of which are those of the triazine, triazole, uracil, urea, amide, diphenylether, carbamate and bipyridylium types.

The herbicidal properties of the subject compounds were discovered in a number of greenhouse tests. The test procedures and results follow.

COMPOUNDS

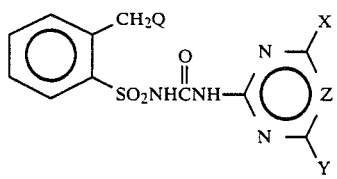

| COMPOUND | Q | X | Y | Z |
|---|---|---|---|---|
| 1 | N-pyrrolidinone (2-oxo) | OCH$_3$ | OCH$_3$ | CH |
| 2 | N-pyrrolidinone (2-oxo) | OCH$_3$ | OCH$_3$ | N |
| 3 | N-oxazolidinone (2-oxo) | CH$_3$ | CH$_3$ | CH |
| 4 | N-oxazolidinone (2-oxo) | OCH$_3$ | OCH$_3$ | CH |
| 5 | N-oxazolidinone (2-oxo) | OCH$_3$ | OCH$_3$ | N |
| 6 | N-(5-methyl-1,3,4-oxadiazol-2(3H)-on-3-yl) | CH$_3$ | CH$_3$ | CH |
| 7 | N-(5-methyl-1,3,4-oxadiazol-2(3H)-on-3-yl) | CH$_3$ | OCH$_3$ | CH |
| 8 | N-(5-methyl-1,3,4-oxadiazol-2(3H)-on-3-yl) | Cl | OCH$_3$ | CH |
| 9 | 5-methyl-γ-butyrolactone | CH$_3$ | OCH$_3$ | CH |
| 10 | 5-methyl-γ-butyrolactone | CH$_3$ | OCH$_3$ | N |
| 11 | 5-methyl-γ-butyrolactone | CH$_3$ | OCH$_3$ | N |
| 12 | 5-methyl-γ-butyrolactone | CH$_3$ | OCH$_3$ | OCH$_3$ | CH |

-continued
COMPOUNDS (thiophene-based structure with SO$_2$NHCNH-pyrimidine, CH$_2$Q substituent)

| COMPOUND | Q | X | Y | Z |
|---|---|---|---|---|
| 13 | N-pyrrolidinone (2-oxo) | CH$_3$ | OCH$_3$ | CH |
| 14 | N-pyrrolidinone (2-oxo) | OCH$_3$ | OCH$_3$ | CH |
| 15 | N-pyrrolidinone (2-oxo) | Cl | OCH$_3$ | CH |
| 16 | N-oxazolidinone (2-oxo) | CH$_3$ | CH$_3$ | CH |
| 17 | N-oxazolidinone (2-oxo) | CH$_3$ | OCH$_3$ | CH |
| 18 | N-oxazolidinone (2-oxo) | OCH$_3$ | OCH$_3$ | CH |
| 19 | N-oxazolidinone (2-oxo) | Cl | OCH$_3$ | CH |
| 20 | N-oxazolidinone (2-oxo) | CH$_3$ | OCH$_3$ | N |

COMPOUNDS -continued

| # | Structure | R1 | R2 | R3 |
|---|---|---|---|---|
| 21 | -N(C(=O)CH3)-O-N= (ring) | CH3 | OCH3 | CH |
| 22 | -N(C(=O)OCH3)-O-N= (ring) | OCH3 | OCH3 | CH |

Test A

Seeds of crabgrass (Digitaria, spp.), barnyard-grass (*Echinochloa crusgalli*), wild oats (*Avena fatua*), cheatgrass (*Bromus secalinus*), velvetleaf (*Abutilon theophrasti*), morningglory (Ipomoea spp.), cocklebur (*Xanthium pensylvanicum*), sorghum, corn, soybean, sugarbeet, cotton, rice, wheat, and purple nutsedge (*Cyperus rotundus*) tubers were planted and treated preemergence with the test chemicals dissolved in a non-phytotoxic solvent. At the same time, these crop and weed species were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

C=chlorosis/necrosis;
B=burn;
D=defoliation;
E=emergence inhibition;
G=growth retardation;
H=formative effect;
U=unusual pigmentation;
X=axillary stimulation;
S=albinism; and
6Y=abscised buds or flowers.

TABLE A

| | Cmpd. 1 | Cmpd. 2 | Cmpd. 3 |
|---|---|---|---|
| Rate (kg/ha) | 0.05 | 0.05 | 0.05 |
| POSTEMERGENCE | | | |
| Morningglory | 10C | 1C,1H | 9C |
| Cocklebur | 10C | 1C | 5C,9G |
| Velvetleaf | 9C | 0 | 2C,6G |
| Nutsedge | 3C,8G,9X | 0 | 5G |
| Crabgrass | 4C,9G | 0 | 5C,9G |
| Barnyardgrass | 9C | 0 | 9C |
| Cheatgrass | 9C | 0 | 8G |
| Wild Oats | 4C,8G | 2C,2H | 9C |
| Wheat | 3G | 0 | 9C |
| Corn | 5U,9G | 8G | 10C |
| Soybean | 9C | 3C | 9C |
| Rice | 9C | 5G | 6C,9G |
| Sorghum | 9C | 4G | 9C |
| Sugar Beets | 9C | 3C,3H | 9C |
| Cotton | 9C | 2C,2H | 5C,9G |
| PREEMERGENCE | | | |
| Morningglory | 9G | 2H | 8H |
| Cocklebur | 9H | 2H | 9H |
| Velvetleaf | 9C | 7G | 7G |
| Nutsedge | 8G | 0 | 4G |
| Crabgrass | 2C,6G | 2G | 2G |
| Barnyardgrass | 4C,9H | 2G | 2C,9H |
| Cheatgrass | 5C,9H | 0 | 7H |
| Wild Oats | 4C,9G | 0 | 9C |
| Wheat | 4C,8G | 0 | 9H |
| Corn | 4C,9H | 2G | 4C,9H |
| Soybean | 3C,7G | 0 | 5G |
| Rice | 10E | 0 | 10E |
| Sorghum | 10E | 0 | 10E |
| Sugar Beets | 5C,9G | | 10E |
| Cotton | 4C,9G | 0 | 8G |

| | Cmpd. 4 | Cmpd. 5 | Cmpd. 6 |
|---|---|---|---|
| Rate (kg/ha) | 0.05 | 0.05 | 0.05 |
| POSTEMERGENCE | | | |
| Morningglory | 10C | 2C,6G | 2C,5G |
| Cocklebur | 9C | 2C,3H | 3C,9H |
| Velvetleaf | 10C | 0 | 3G |
| Nutsedge | 3C,9G | 0 | 2C,4G |
| Crabgrass | 3C,9H | 0 | |
| Barnyardgrass | 9C | 3C 8H | 3C,5H |
| Cheatgrass | 7G | 0 | 6G |
| Wild Oats | 4C,8G | 4C,8G | 6G |
| Wheat | 0 | 0 | 4G |
| Corn | 6C,9G | 5C,9G | 3C,7H |
| Soybean | 6C,9G | 4C,8G | 5C,9G |
| Rice | 9C | 4C,8G | 5G |
| Sorghum | 5C,9G | 3C,6H | 4C,8H |
| Sugar Beets | 9C | 4C,7G | 2H |
| Cotton | 9C | 4C,6G | 4C,8H |
| PREEMERGENCE | | | |
| Morningglory | 9G | 3G | 7H |
| Cocklebur | 9H | 3G | 2H |
| Velvetleaf | 8G | 0 | 3G |
| Nutsedge | 9G | 8G | 0 |
| Crabgrass | 9G | 0 | 4G |
| Barnyardgrass | 5C,9H | 2C | 0 |
| Cheatgrass | 2C,7G | 0 | 7G |
| Wild Oats | 3C,8G | 0 | 0 |
| Wheat | 7G | 0 | 0 |
| Corn | 3U,9H | 2C,5G | 0 |
| Soybean | 4C,8H | 2G | 10E |
| Rice | 10E | 7G | 0 |
| Sorghum | 4C,9H | 2C,6G | 3G |
| Sugar Beets | 10C | 10C | 8G |
| Cotton | 5C,9G | 0 | 0 |

| | Cmpd. 7 | Cmpd. 8 |
|---|---|---|
| Rate (kg/ha) | 0.05 | 0.05 |
| POSTEMERGENCE | | |
| Morningglory | 5C,9G | 4C,9G |
| Cocklebur | 6C,9G | 5C,9G |
| Velvetleaf | 3C,8H | 5G |
| Nutsedge | 5G | 2G |
| Crabgrass | 3G | 0 |
| Barnyardgrass | 3C,8H | 0 |
| Cheatgrass | 2C,8G | 0 |
| Wild Oats | 2C,5G | 0 |
| Wheat | 2C,5G | 0 |
| Corn | 3C,9G | 0 |
| Soybean | 9C | 3C,8G |
| Rice | 3C,8G | 5G |
| Sorghum | 2C,9G | 3C,7G |
| Sugar Beets | 3C,5G | 2H |
| Cotton | 3C,6G | 5G |
| PREEMERGENCE | | |
| Morningglory | 9G | 3G |
| Cocklebur | 9H | 9G |
| Velvetleaf | 9C | 0 |
| Nutsedge | 3G | 0 |
| Crabgrass | 2G | 0 |
| Barnyardgrass | 2C,5G | 0 |
| Cheatgrass | 8G | 0 |
| Wild Oats | 2C,6G | 0 |
| Wheat | 7G | 2G |
| Corn | 2C,8H | 2G |
| Soybean | 3C,6H | 2H |
| Rice | 3C,7H | 0 |
| Sorghum | 3C,9H | 2C |
| Sugar Beets | 4C,9G | 6G |
| Cotton | 5G | 0 |

| | Cmpd. 9 | Cmpd. 10 | Cmpd. 11 |
|---|---|---|---|

TABLE A-continued

| Rate kg/ha | 0.05 | 0.05 | 0.05 |
|---|---|---|---|
| POSTEMERGENCE | | | |
| Morningglory | 10C | 4C,8G | 6C,9G |
| Cocklebur | 10C | 4C,9G | 4C,9G |
| Velvetleaf | 4C,9G | 4C,8H | 4C,9G |
| Nutsedge | 0 | 0 | 0 |
| Crabgrass | 3G | 0 | 0 |
| Giant Foxtail | 4G | 0 | 0 |
| Barnyardgrass | 2C,8G | 1C | 0 |
| Cheatgrass | 2C,8G | 0 | 0 |
| Wild Oats | 5G | 0 | 0 |
| Wheat | 4G | 0 | 0 |
| Corn | 3C,7G | 1H | 0 |
| Barley | 2C,7G | 0 | 0 |
| Soybean | 5H | 0 | 0 |
| Rice | 7G | 0 | 2G |
| Sorghum | 2C,9G | 2C,5G | 4G |
| Sugar beet | 3C,7G | 9C | 9C |
| Cotton | 9C | 8G | 2C,9G |
| PREEMERGENCE | | | |
| Morningglory | 9G | 5G | 9C |
| Cocklebur | — | 9H | — |
| Velvetleaf | 10C | 9C | 2G |
| Nutsedge | 0 | 0 | 0 |
| Crabgrass | 7G | 0 | 0 |
| Giant Foxtail | 5G | 0 | 0 |
| Barnyardgrass | 2C,8G | 2C | 0 |
| Cheatgrass | 7G | 0 | 0 |
| Wild Oats | 5G | 0 | 0 |
| Wheat | 5G | 0 | 0 |
| Corn | 2C,7G | 0 | 0 |
| Barley | 8G | 0 | 0 |
| Soybean | 2G | 2G | 2C,5G |
| Rice | 7G | 2G | 0 |
| Sorghum | 2C,8G | 3G | 4G |
| Sugar beet | 8G | 7G | 4C,8G |
| Cotton | 7G | 4G | 5G |

| | Compound 12 | Cmpd. 13 | Cmpd. 14 |
|---|---|---|---|
| Rate kg/ha | 0.05 | 0.01 | 0.05 | 0.05 |
| POSTEMERGENCE | | | | |
| Morningglory | 9C | 2G | 10C | 10C |
| Cocklebur | 10C | 2C,9H | 9C | 9C |
| Velvetleaf | 10C | 5C,9G | 4C,8G | 9C |
| Nutsedge | 6G | 2G | 4G | 4C,8G |
| Crabgrass | 0 | 0 | 0 | 0 |
| Giant Foxtail | 2G | 0 | 4G | 4C,9G |
| Barnyardgrass | 7G | 3H | 8H | 10C |
| Cheatgrass | 7G | 6G | 0 | 7G |
| Wild Oats | 0 | 0 | 3C,6G | 0 |
| Wheat | 5G | 0 | 4G | 0 |
| Corn | 1H | 0 | 3C,8H | 9G |
| Barley | 7G | 3G | 0 | 2C |
| Soybean | 2C,8G | 5H | 5C,9G | 9C |
| Rice | 8G | 3G | 2C,6G | 2C,9G |
| Sorghum | 2C,8H | 7G | 3C,8H | 4C,9G |
| Sugar beet | 9C | 5C,9G | 10C | 10C |
| Cotton | 3C,9G | 4C,8G | 5C,9G | 9C |
| PREEMERGENCE | | | | |
| Morningglory | 5G | 5G | 8G | 9G |
| Cocklebur | — | 7G | 9H | 9H |
| Velvetleaf | 7G | 6G | 9G | 9G |
| Nutsedge | 4G | 0 | 0 | 5G |
| Crabgrass | 0 | 0 | 4G | — |
| Giant Foxtail | 4G | 2C | 2G | 6G |
| Barnyardgrass | 2C,7G | 2C | 2G | 8G |
| Cheatgrass | 9H | 7G | 0 | 7G |
| Wild Oats | 0 | 0 | 0 | 0 |
| Wheat | 0 | 0 | 0 | 0 |
| Corn | 6G | 5G | 3C,7H | 3C,8G |
| Barley | 7G | 0 | 0 | 5G |
| Soybean | 0 | 0 | 3C,7H | 9H |
| Rice | 6G | 0 | 3G | 6G |
| Sorghum | 2C,8H | 3G | 4G | 4C,9H |
| Sugar beet | 8G | 5G | 10C | 10C |
| Cotton | 5G | — | 3C,7G | 9G |

| | Cmpd. 15 | Cmpd. 16 | Cmpd. 17 | Cmpd. 18 |
|---|---|---|---|---|
| Rate kg/ha | 0.05 | 0.05 | 0.05 | 0.05 |
| POSTEMERGENCE | | | | |
| Morningglory | 5C,9G | 10C | 10C | 10C |
| Cocklebur | 5C 9H | 10C | 10C | 10C |
| Velvetleaf | 2G | 5G | 4C,9G | 9C |
| Nutsedge | 0 | 2C,9G | 3C,7G | 5C,9G |
| Crabgrass | 0 | 6G | 2G | 3G |
| Giant Foxtail | 0 | 5C,9G | 4C,8G | 3C,8G |
| Barnyardgrass | 5H | 10C | 4C,9H | 4C,9H |
| Cheatgrass | 0 | 9G | 7G | 4C,9G |
| Wild Oats | 0 | 3G | 0 | 0 |
| Wheat | 0 | 3G | 3G | 0 |
| Corn | 4G | 9C | 9C | 10C |
| Barley | 0 | 2C,5G | 0 | 0 |
| Soybean | 3C,8G | 4C,9G | 4C,9G | 9C |
| Rice | 6G | 9C | 5C,9G | 8G |
| Sorghum | 4C,9H | 4C,9G | 4C,9H | 9H |
| Sugar beet | 4C,8G | 10C | 10C | 10C |
| Cotton | 3C,7G | 4C,9G | 10C | 10C |
| PREEMERGENCE | | | | |
| Morningglory | 8G | 9G | 9G | 9G |
| Cocklebur | — | 9H | 9H | 9H |
| Velvetleaf | 7G | 9G | 9G | 9G |
| Nutsedge | 0 | 9G | 8G | 10E |
| Crabgrass | — | 6G | 5G | 5G |
| Giant Foxtail | 3G | 3C,7G | 3C,7G | 3C,7G |
| Barnyardgrass | 2G | 3C,9H | 4C,9H | 9H |
| Cheatgrass | 0 | 8G | 8G | 9H |
| Wild Oats | 0 | 5G | 5G | 4G |
| Wheat | 0 | 4G | 2G | 0 |
| Corn | 3G | 9H | 3C,9H | 3C,9H |
| Barley | 0 | 2C,8G | 5G | 6G |
| Soybean | 0 | 7H | 9H | 9H |
| Rice | 3G | 4C,8H | 8G | 8G |
| Sorghum | 0 | 8G | 3C,8G | 7G |
| Sugar beet | 8G | 10E | 10E | 10E |
| Cotton | 8G | 9G | 9G | 9G |

| | Cmpd. 19 | Cmpd. 20 | Cmpd. 21 | Cmpd. 22 |
|---|---|---|---|---|
| Rate kg/ha | 0.05 | 0.05 | 0.05 | 0.05 |
| POSTEMERGENCE | | | | |
| Morningglory | 10C | 4C,8H | 10C | 4C,9G |
| Cocklebur | 10C | 4C,9G | 9C | 4C,9H |
| Velvetleaf | 3C,7G | 3C,7H | 4C,8G | 4C,8G |
| Nutsedge | 4G | 0 | 2C | 2G |
| Crabgrass | 3G | 0 | 3G | 2G |
| Giant Foxtail | 3C,5G | 2C,8G | 2G | 0 |
| Barnyardgrass | 3C,8H | 5C,9H | 2C,5H | 0 |
| Cheatgrass | 3C,6G | 0 | 0 | 0 |
| Wild Oats | 0 | 0 | 0 | 0 |
| Wheat | 2G | 0 | 0 | 0 |
| Corn | 9H | 10C | 8H | 3H |
| Barley | 0 | 0 | 0 | 0 |
| Soybean | 4C,9G | 2C,7G | 4C,9G | 4C,9G |
| Rice | 8G | 7G | 5G | 4G |
| Sorghum | 4C,9H | 4C,9H | 3C,8G | 2G |
| Sugar beet | 9C | 4C,8H | 3C,7G | 2C,6G |
| Cotton | 10C | 3C,7G | 4C,8H | 3C,6G |
| PREEMERGENCE | | | | |
| Morningglory | 8G | 7H | 9G | 7H |
| Cocklebur | 8H | 7G | 9H | 7H |
| Velvetleaf | 9G | 0 | 8G | 7G |
| Nutsedge | 9G | 0 | 0 | 0 |
| Crabgrass | 2G | 0 | 3G | — |
| Giant Foxtail | 2C,4G | 0 | 3G | 0 |
| Barnyardgrass | 3C,7G | 0 | 0 | 0 |
| Cheatgrass | 5G | 0 | 0 | 0 |
| Wild Oats | 0 | 0 | 0 | 0 |
| Wheat | 0 | 0 | 0 | 0 |
| Corn | 7G | 7G | 5G | 0 |
| Barley | 0 | 0 | 0 | 0 |
| Soybean | 0 | 0 | 3C,6H | 2C,4H |
| Rice | 5G | 5G | 2C,5G | 0 |
| Sorghum | 6G | 0 | 2C,4G | 2C |
| Sugar beet | 4C,9G | 9C | 8G | 8G |
| Cotton | 2C,8G | 4G | 2C,6G | 7G |

REFERENCES

1. Scott and Kearse, *J.Org. Chem.*, 5, 598 (1940).
2. Jones et. al., *J. Am. Chem. Soc.*, 48, 181 (1926).
3. Jones et. al., *IBID.*, 49, 2528 (1927).

4. Z. N. Parnes et al., *Izv. Akad. Nauk SSSR, Ser. Khim.*, (11) 2526 (1977); *CA.*, 88 62239k.
5. E. Spath and F. Kuffner., *Ber.*, 68, 2238 (1936).
6. D. S. Tarbell and C. Weaver, *J. Am. Chem. Soc.*, 63, 2939 (1941).
7. H. O. House, "Modern Synthetic Reactions," 2nd Ed., W. A. Benjamin, FNC., Menlo Park, 1972, pp. 334-335 and references cited within.
8. B. M. Trost and T. H. Salzmann, *J. Am. Chem. Soc.*, 95, 6840 (1973). This procedure can be utilized for the synthesis of α, β-unsaturated lactams, sulfones and sultams. Literature procedures for the formation of α-anions of the above active methylene compounds are incorporated in table 2 where pertinent.
9. C. V. Wilson and J. F. Stenberg, *Org. Syn.*, Coll. Vol. 4, 564 (1963).
10. T. Satoh, S. Suzuki, Y. Suzuki, Y. Miyaji and Z. Imai, *Tet. Lett.*, (52) 4555 (1969).
11. A. C. Cope and E. Ciganek, *Org. Syn.*, Coll. Vol. 4, 339 (1963).
12. S. L. Friess, *J. Am. Chem. Soc.*, 71, 2571 (1949).
13. S. L. Friess and P. E. Frankenburg, *Ibid.*, 74, 2679 (1952).
14. C. H. Hassall, *Org. Reactions*, 9, 73 (1957).
15. Borsche, *Ber.*, 48, 682 (1915).
16. *Ibid.*, 56, 2012, 2132 (1923).
17. *Ibid.*, 59, 237 (1926).
18. Cawley and Plant, *J. Chem. Soc.*, 1214 (1938).
19. Attenburrow, et. al.,·*Ibid.*, 571 (1945).
20. E. Winterfeldt, *Ber Deutsch Chem Ges.*, 97, 2463 (1964).
21. J. Hebky and J. Kejha, *CA*, 50, 155326.
22. J. V. Greenhill, *Chem. Soc. Rev.*, 6, 277 (1977).
23. J. A. Leben, *Ber.*, 29, 1673, (1896).
24. Von Pechmann and W. Welsh, *Ber.*, 17, 2391 (1884).
25. J. H. Boyer and W. Schoen, *Org. Syntheses*, Coll. Vol. IV, 532 (1963).
26. H. Hiari and K. Miyata, *J. Patent* 72, 42,832, Jan. 28, 1970.
27. D. E. Heitmeier, J. T. Hortenstine Jr., and A. P. Gray, *J. Org. Chem.*, 36, 1449 (1971).
28. T. S. Hamilton and R. J. Adams, *J. Am. Chem. Soc.*, 50, 2260 (1928).
29. J. L. Herrmann and R. H. Schlessinger, *J. Am. Chem. Soc., Chem. Comm.*, 711 (1973).
30. G. H. Posner and G. L. Lomis, *Chem. Comm.*, 892 (1972).
31. K. Iwai, *Chem. Lett.*, 385 (1974).
32. P. Hullot et. al., *Can. J. Chem.*, 54, 1098 (1976).
33. P. A. Zoretic and F. Barcelos, *Tet. Lett.*, 529 (1977).
34. B. M. Trost and R. A. Kunz, *J. Org. Chem.*, 34 (1974).
35. J. P. Depres, A. E. Greene and P. Crabbe, *Tet. Lett.*, 2191 (1978).
36. J. K. Crandall and A. C. Clark, *Tet. Lett.*, 325-28 (1969). ·
37. J. B. Bush and H. Finkbiener, *J. Am. Chem. Soc.*, 90, 5903 (1968).
38. H. O. House, "Modern Synthetic Reactions," 2nd Ed., W. A. Benjamin, Inc., Menlo Park, 1972. pp. 492-628 and references cited within.
39. N. C. Corbin, P. Fraher, and J. D. McChesney, *J. Pharm. Science*, 68, 1501 (1979).
40. Gor, Harmon, Levisalles and Wagnon, *Chem. Comm.*, 88 (1973).
41. G. H. Posner, *Org. Reactions*, 19, 1 (1972).
42. H. O. House, *Acc. Chem. Res.*, 9 (1976).
43. Truce, Hollister, Lindy and Parr, *J. Org. Chem.*, 33, 43 (1968).
44. Truce and Vrencur, *J. Org. Chem.*, 35, 1226 (1970).
45. M. Julia and Arnould, *Bull. Soc. Chim. Fr.*, 743, 746 (1973).
46. A. D. Bliss, W. K. Cline, C. E. H. Milton and O. J. Sweeting, *J. Org. Chem.*, 28, 3537 (1963).
47. H. D. Hartough, "Chemistry of Heterocyclic Compounds," 3, Interscience Publishers, Inc., New York (1952).
48. A. Williams, ♭Furans Synthesis and Applications," Noyes Data Corp., New Jersey, 1973.
49. M. E. Garst, J. N. Bonfiglio, D. A. Grudoski, and J. Marks, *Tet. Lett.*, 2671 (1978).
50. Wolf and Folkers, *Org. Reactions*, 6, 443-468 (1951).
51. G. Stork and L. Maldonado, *J. Am. Chem. Soc.*, 73, 5286 (1971).
52. G. Stork and L. Maldonado, *Ibid.*, 76, 5272 (1974).
53. R. Woodward and Eastman, *j. Am. Chem. Soc.*, 68, 2229 (1946).
54. R. Woodward and Eastman, *Ibid.*, 66, 849 (1944).
55. V. Luhmann and W. Luttke, *Chem. Ber.*, 105, 1350 (1972).
56. I. J. Borowitz and G. J. Williams, *J. Org. Chem.*, 32, 4157 (1967).
57. J. March, "Advanced Organic Chemistry," 2nd Ed., McGraw Hill Book Company, New York, 1977, pp. 363-365.
58. R. Gorski, G. J. Wolber and J. Wemple, *Tet. Lett.*, 2577 (1976).
59. T. A. Morgan and B. Ganem, *Tet. Lett.*, 2773 (1980).
60. M. Koreeda and H. Akagi, *Tet. Lett.*, 1197 (1980).
61. N. Sugiyama, M. Yamamoto and C. Kashima, *Bull. Chem. Soc. Japan*, 42, 1357 (1969).
62. G. M. Bennett and L. V. D. Scorah, *J. Chem. Soc.*, 194 (1927).
63. A. Belanger and P. Brassard, *Chem. Comm.*, 863 (1972).
64. J. Fried, "Heterocyclic Compounds," ed. by R. C. Elderfield, Wiley, New York, 1950, Vol. 1, pp. 358-370.
65. L. F. Cavalieri, *Chem. Rev.*, 41, (525) (1947).
66. E. Tihanyi, M. Gai, and P. Dvortsak, *Heterocycles*, 20, 571 (1983).
67. Y. Kurasawa, M. Ichikawa, A. Sakukura and H. Takada, *Chem. Pharm. Bull., Tokyo*, 32, 4140 (1984).
68. *Ibid.*, 30, 336 (1982).
69. K. Takacs and K. Harsanyi, *Chem. Ber.*, 103, 2330 (1970).
70. P. W. Searle and W. K. Warburton, *J. Chem. Soc., Perkins Trans.*, 1, 85 (1974).
71. A. R. Katritzky, B. Wallis, R. T. C. Brownlee, and R. D. Topsom. *Tet.*, 21, 1681 (1965).
72. S. Kubota and M. Uda, *Chem. Pharm. Bull.*, 21, 1342, (1973).
73. S. Kubuta and M. Uda, *Ibid.*, 24, 1336 (1976).
74. R. K. Howe, T. A. Gruner, L. G. Carter, L. L. Black, and J. E. Franz, *J. Org. Chem.* 43, 3736 (1978).
75. R. Boyle, F. Eloy and R. Lenaers, *Helv. Chim. Acta.*, XLVI, 1073 (1973).
76. J. Sauer and K. K. Mayer, *Tet. Lett.*, 319 (1968).
77. G. Beck, *Chem. Ber.*, 84, 688 (1951).
78. J. Goerdeler and R. Sappelt, *Chem. Ber.*, 100, 2064 (1967).
79. T. J. Giacobbe, *J. Het. Chem.* 15, 1227 (1978).
80. Kurt Pilgram, *Ibid.*, 19, 823 (1982).
81. M. Kishi, H. Ishitobi, W. Nagata, and T. Tsuji, *Heterocycles*, 13 197 (1979).

82. A. K. Saund and M. K. Mathur, *Int. J. Peptide Protein Res.*, 5, 7, (1964).
83. Y. Fuju Moto et. al., *Heterocycles,* 6, 1604 (1977).
84. For a discussion of the optimal conditions required for selectively generating thermodynamic or kinetic enolates, see J. C. Stowell, "Carbanions in Organic Synthesis," John Wiley and Sons, Inc., New York, 1979, pp. 8–11 and references cited therein.

What is claimed is:

1. A compound of which is

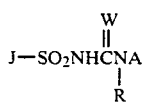

wherein

J is

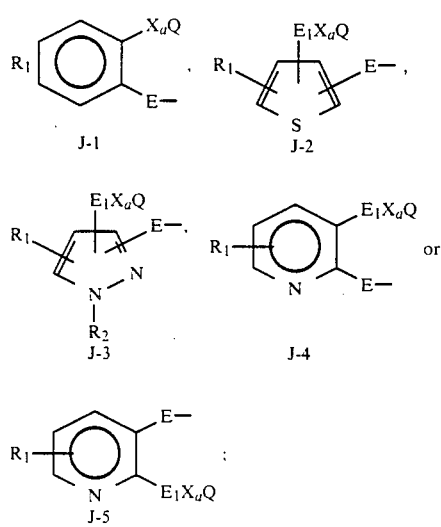

W is O or S;
R is H or $CH_3$;
$E_1$ is O, S, SO, $SO_2$ or a single bond.
$X_a$ is $CH_2$, $CH(CH_3)$, $CH_2CH_2$, $CH_2CH_2CH_2$ or CO;
E is a single bond, $CH_2$ or O;
Q is selected from

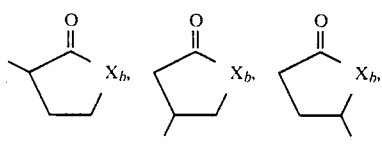

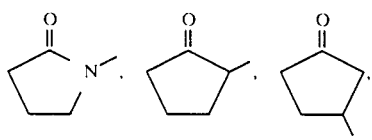

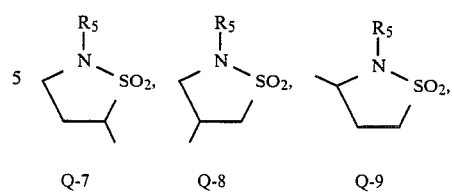

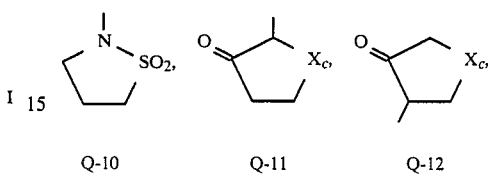

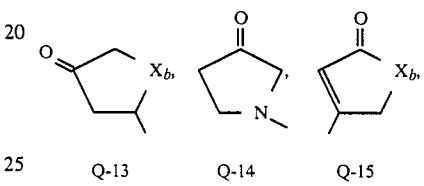

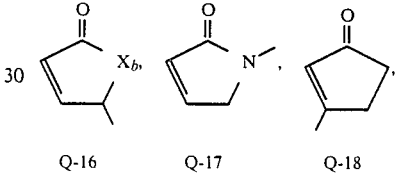

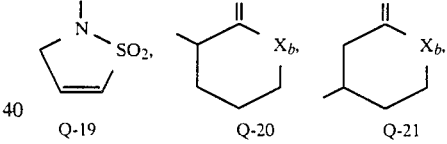

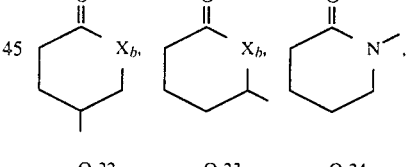

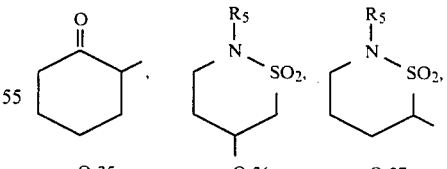

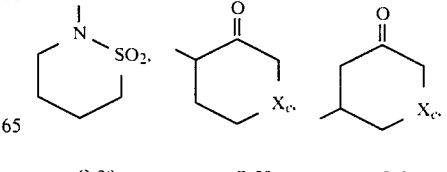

-continued
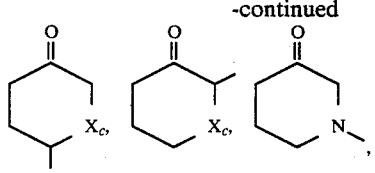
Q-31    Q-32    Q-33
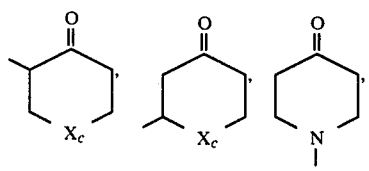
Q-34    Q-35    Q-36
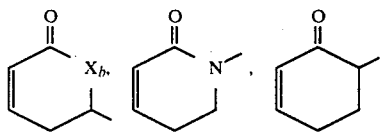
Q-37    Q-38    Q-39
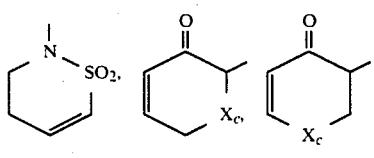
Q-40    Q-41    Q-42
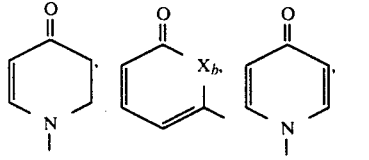
Q-43    Q-44    Q-45
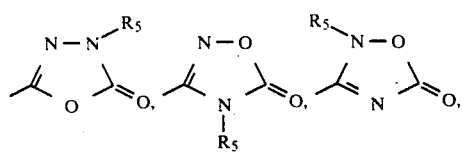
Q-46    Q-47    Q-48
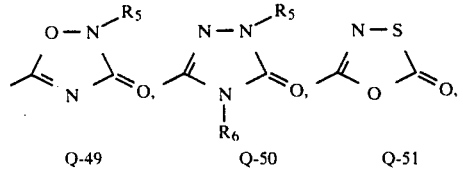
Q-49    Q-50    Q-51
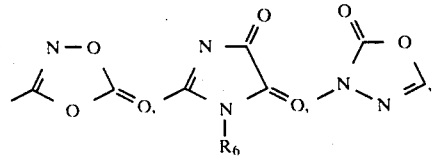
Q-52    Q-53    Q-54
-continued
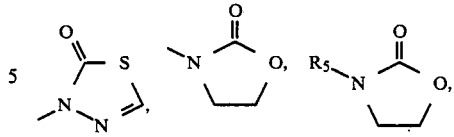
Q-55    Q-56    Q-57
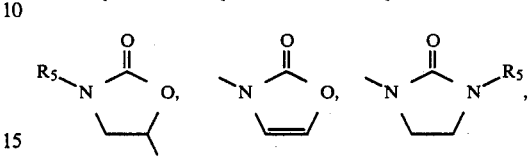
Q-58    Q-59    Q-60
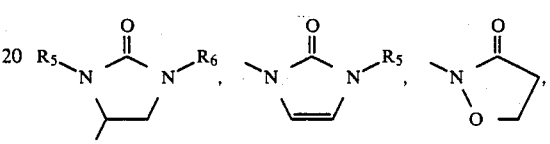
Q-61    Q-62    Q-63
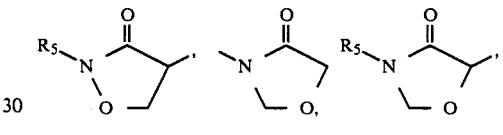
Q-64    Q-65    Q-66
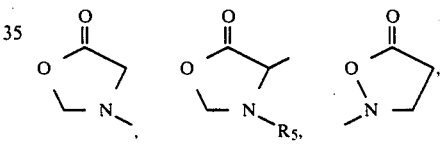
Q-67    Q-68    Q-69
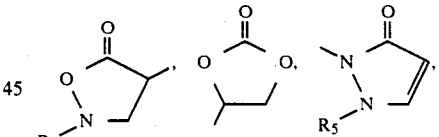
Q-70    Q-71    Q-72
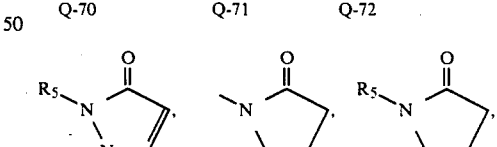
Q-73    Q-74    Q-75
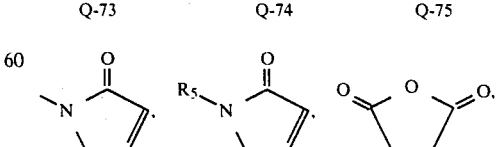
Q-76    Q-77    Q-78

-continued

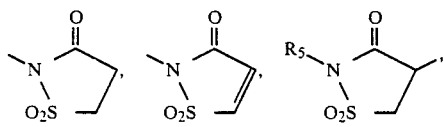

Q-79  Q-80  Q-81

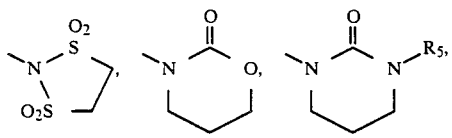

Q-82  Q-83  Q-84

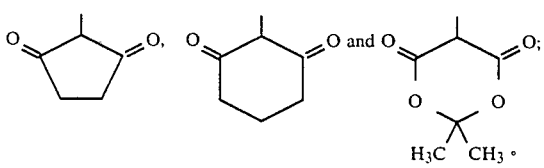

Q-85  Q-86  Q-87 wherein
Q-1 through Q-87 may be optionally substituted with 1 or 2 groups selected from $C_1-C_2$ alkyl or $C_1-C_2$ haloalkyl;
$R_5$ and $R_6$ are independently H or $C_1-C_3$ alkyl;
$X_b$ is O or $NR_5$; and
$X_c$ is O, S, SO, $SO_2$ or $NR_5$.
$R_1$ is H, $C_1-C_3$ alkyl, $C_1-C_3$ haloalkyl, halogen, nitro, $C_1-C_3$ alkoxy, $SO_2NR_aR_b$, $C_1-C_3$ alkylthio, $C_1-C_3$ alkylsulfinyl, $C_1-C_3$ alkylsulfonyl, $CH_2CN$, CN, $CO_2R_c$, $C_1-C_3$ haloalkoxy, $C_1-C_3$ haloalkylthio, $C_2-C_4$ alkoxyalkyl, $C_2-C_4$ alkylthioalkyl, $CH_2N_3$ or $NR_dR_e$;
$R_a$ is H, $C_1-C_4$ alkyl, $C_2-C_3$ cyanoalkyl, methoxy or ethoxy;
$R_b$ is H, $C_1-C_4$ alkyl or $C_3-C_4$ alkenyl; or
$R_a$ and $R_b$ may be taken together as $-(CH_2)_3-$, $-(CH_2)_4-$, $-(CH_2)_5-$ or $-CH_2CH_2OCH_2CH_2-$;
$R_c$ is $C_1-C_4$ alkyl, $C_3-C_4$ alkenyl, $C_3-C_4$ alkynyl, $C_2-C_4$ haloalkyl, $C_2-C_3$ cyanoalkyl, $C_5-C_6$ cycloalkyl, $C_4-C_7$ cycloalkylalkyl or $C_2-C_4$ alkoxyalkyl;
$R_d$ and $R_e$ are independently H or $C_1-C_2$ alkyl;
A is

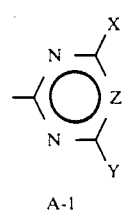

A-1 or

-continued

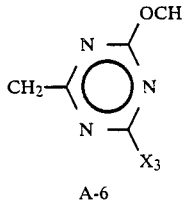

A-6

X is H, $C_1-C_4$ alkyl, $C_1-C_4$ alkoxy, $C_2-C_4$ haloalkoxy, $C_1-C_4$ haloalkyl, $C_1-C_4$ haloalkylthio, $C_1-C_4$ alkylthio, $C_2-C_5$ alkoxyalkyl, $C_2-C_{C5}$ alkoxyalkoxy, amino, $C_1-C_3$ alkylamino, di($C_1-C_3$ alkyl)amino or $C_3-C_5$ cycloalkyl;
Y is H, $C_1-C_4$ alkyl, $C_1-C_4$ alkoxy, $C_2-C_4$ haloalkoxy, $C_1-C_4$ haloalkylthio, $C_1-C_4$ alkylthio, $C_2-C_5$ alkoxyalkyl, $C_2-C_5$ alkoxyalkoxy, amino, $C_1-C_3$ alkylamino, di($C_1-C_3$ alkyl)amino, $C_3-C_4$ alkenyloxy, $C_3-C_4$ alkynyloxy, $C_2-C_5$ alkylthioalkyl, $C_1-C_4$ haloalkyl, $C_2-C_4$ alkynyl, azido, cyano, $C_2-C_5$ alkylsulfinylalkyl, $C_2-C_5$ alkylsulfonylalkyl,

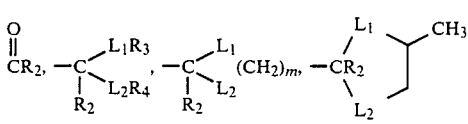

or $N(OCH_3)CH_3$;
m is 2 or 3;
$L_1$ and $L_2$ are independently O or S;
$R_2$ is H or $C_1-C_3$ alkyl;
$R_3$ and $R_4$ are independently $C_1-C_3$ alkyl;
Z is N, and;
$X_3$ is $CH_3$ or $OCH_3$;
and their agriculturally suitable salts; provided that
(a) when Q contains 2 heteroatoms selected from 0-2 oxygen and 0-2 sulfur, said heteroatoms are not bonded directly to one another unless in the form $O-SO_2$, and when Q contains 3 nitrogen heteroatoms, only two of these may be bonded directly together;
(b) when J is J-2 or J-3, the substituent $E_1X_aQ$ and the sulfonylurea bridge are on adjacent carbon atoms;
(c) when E is O, then J is J-1 and W is O;
(d) when W is S, then R is H, A is A-1, and Y is $CH_3$, $OCH_3$, $OC_2H_5$, $CH_2OCH_3$, $C_2H_5$, $CF_3$, $SCH_3$, $OCH_2CH=CH_2$, $OCH_2C\equiv CH$, $OCH_2CH_2OCH_3$, $CH(OCH_3)_2$ or 1,3-dioxolan-2-yl;
(e) when the total number of carbon atoms of X and Y is greater than four, then the number of carbons of $R_1$ must be less than or equal to two, and the number of carbons of the substituent on Q must also be less than or equal to two;
(f) when A is A-1 and J is J-1 wherein E is a single bond, $X_a$ is $CH_2$, $CH(CH_3)$ or $CH_2CH_2$ and Q is a 5-membered heterocyclic ring containing one endocyclic double bond or a 6-membered heterocyclic ring containing 1 or 2 endocyclic double bonds which is unsubstituted or substituted by one or more $C_1-C_4$ alkyl groups then said heterocycle must contain at least one nitrogen and be bound to $X_a$ through nitrogen; and
(g) when $X_a$ is CO then $E_1$ is a single bond.
2. The compound of formula I of claim 1 wherein
$E_1$ is a single bond;
$X_a$ is $CH_2$, $CH(CH_3)$, $CH_2CH_2$ or $CH_2CH_2CH_2$; and $R_1$ is H, $C_1$-$C_3$ alkyl, $C_1$-$C_3$ haloalkyl, halogen, nitro, $C_1$-$C_3$ alkoxy, $SO_2NR_aR_b$, $C_1$-$C_3$ alkylthio, $C_1$-$C_3$ alkylsulfinyl, $C_1$-$C_3$ alkylsulfonyl, $CH_2CN$, CN, $CO_2R_c$, $C_1$-$C_3$ haloalkoxy or $C_1$-$C_3$ haloalkylthio.

3. The compounds of Formula I of claim 1 wherein E is a single bond.

4. The compounds of Formula I of claim 1 where E is $CH_2$, W is O, and $E_1$ is a single bond.

5. The compounds of Formula I of claim 1 where E is O and $E_1$ is a single bond.

6. The compounds of claim 1 wherein
$E_1$ is a single bond;
$X_a$ is $CH_2$ or $CH_2CH_2$;
R is H;
W is O;
$R_1$ is H, F, Cl, Br, $C_1$-$C_2$ alkyl, $C_1$-$C_3$ alkoxy, $C_1$-$C_3$ alkylthio, or $C_1$-$C_2$ alkyl, $C_1$-$C_3$ alkoxy or $C_1$-$C_3$ alkylthio substituted with 1-3 atoms of F, Cl or Br;
X is $C_1$-$C_2$ alkyl, $C_1$-$C_2$ alkoxy, $CH_2F$, $CF_3$, $OCH_2CH_2F$, $OCH_2CHF_2$, $OCH_2CF_3$, $CH_2Cl$ or $CH_2Br$; and
Y is H, $C_1$-$C_2$ alkyl, $C_1$-$C_2$ alkoxy, $CH_2OCH_3$, $CH_2OCH_2CH_3$, $NHCH_3$, $N(OCH_3)CH_3$, $N(CH_3)_2$, $CF_3$, $SCH_3$, $OCH_2CH=CH_2$, $OCH_2C\equiv CH$, $OCH_2CH_2OCH_3$, $CH_2SCH_3$,

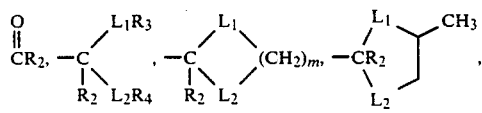

$SCF_2H$, cyclopropyl, $C\equiv CH$ or $C\equiv CCH_3$;

7. The compounds of claim 6 wherein A is A-1.

8. The compounds of claim 7 wherein J is J-1.

9. The compound of claim 1 which is N-[[(4,6-dimethoxy-1,3,5-triazin-2-yl)aminocarbonyl]-2-(2-oxo-1-pyrrolidinylmethyl)benzenesulfonamide.

10. The compound of claim 1 which is N-[(4-methoxy-6-methyl-1,3,5-triazin-2-yl)aminocarbonyl]-2-(2-oxo-3-oxazolidinylmethyl)-3-thiophenesulfonamide.

11. A composition suitable for controlling the growth of undesired vegetation which comprises an effective amount of a compound of claim 1 and at least one of the following: surfactant, solid or liquid diluent.

12. A composition suitable for controlling the growth of undesired vegetation which comprises an effective amount of a compound of claim 2 and at least one of the following: surfactant, solid or liquid diluent.

13. A composition suitable for controlling the growth of undesired vegetation which comprises an effective amount of a compound of claim 3 and at least one of the following: surfactant, solid or liquid diluent.

14. A composition suitable for controlling the growth of undesired vegetation which comprises an effective amount of a compound of claim 4 and at least one of the following: surfactant, solid or liquid diluent.

15. A composition suitable for controlling the growth of undesired vegetation which comprises an effective amount of a compound of claim 5 and at least one of the following: surfactant, solid or liquid diluent.

16. A composition suitable for controlling the growth of undesired vegetation which comprises an effective amount of a compound of claim 6 and at least one of the following: surfactant, solid or liquid diluent.

17. A composition suitable for controlling the growth of undesired vegetation which comprises an effective amount of the compound of claim 7 and at least one of the following: surfactant, solid or liquid diluent.

18. A composition suitable for controlling the growth of undesired vegetation which comprises an effective amount of a compound of claim 8 and at least one of the following: surfactant, solid or liquid diluent.

19. A composition suitable for controlling the growth of undesired vegetation which comprises an effective amount of a compound of claim 9 and at least one of the following: surfactant, solid or liquid diluent.

20. A composition suitable for controlling the growth of undesired vegetation which comprises an effective amount of a compound of claim 10 and at least one of the following: surfactant, solid or liquid diluent.

21. A method for controlling the growth of undesired vegetation which comprises applying to the locus to be protected an effective amount of a compound of claim 1.

22. A method for controlling the growth of undesired vegetation which comprises applying to the locus to be protected an effective amount of a compound of claim 2.

23. A method for controlling the growth of undesired vegetation which comprises applying to the locus to be protected an effective amount of a compound of claim 3.

24. A method for controlling the growth of undesired vegetation which comprises applying to the locus to be protected an effective amount of a compound of claim 4.

25. A method for controlling the growth of undesired vegetation which comprises applying to the locus to be protected an effective amount of a compound of claim 5.

26. A method for controlling the growth of undesired vegetation which comprises applying to the locus to be protected an effective amount of a compound of claim 6.

27. A method for controlling the growth of undesired vegetation which comprises applying to the locus to be protected an effective amount of the compound of claim 7.

28. A method for controlling the growth of undesired vegetation which comprises applying to the locus to be protected an effective amount of a compound of claim 8.

29. A method for controlling the growth of undesired vegetation which comprises applying to the locus to be protected an effective amount of the compound of claim 9.

30. A method for controlling the growth of undesired vegetation which comprises applying to the locus to be protected an effective amount of the compound of claim 10.

* * * * *